United States Patent
Hyde et al.

(10) Patent No.: US 9,864,842 B2
(45) Date of Patent: Jan. 9, 2018

(54) DEVICES, SYSTEMS, AND METHODS FOR AUTOMATED MEDICAL PRODUCT OR SERVICE DELIVERY

(71) Applicant: Elwha LLC, Bellevue, WA (US)

(72) Inventors: Roderick A. Hyde, Redmond, WA (US); Muriel Y. Ishikawa, Livermore, CA (US); Jordin T. Kare, Seattle, WA (US); Gary L. McKnight, Bothell, WA (US); Robert C. Petroski, Seattle, WA (US)

(73) Assignee: ELWHA LLC, Bellevue, WA (US)

( * ) Notice: Subject to any disclaimer, the term of this patent is extended or adjusted under 35 U.S.C. 154(b) by 238 days.

(21) Appl. No.: 14/079,857

(22) Filed: Nov. 14, 2013

(65) Prior Publication Data

US 2015/0134346 A1    May 14, 2015

(51) Int. Cl.
*G06F 19/00* (2011.01)
*G06Q 50/22* (2012.01)
*G06Q 10/08* (2012.01)

(52) U.S. Cl.
CPC ....... *G06F 19/3462* (2013.01); *G06Q 10/087* (2013.01); *G06Q 50/22* (2013.01)

(58) Field of Classification Search
None
See application file for complete search history.

(56) References Cited

U.S. PATENT DOCUMENTS

| | | | |
|---|---|---|---|
| 4,703,756 A | 11/1987 | Gough et al. | |
| 5,338,625 A | 8/1994 | Bates et al. | |
| 5,372,136 A | 12/1994 | Steuer et al. | |
| 5,571,152 A | 11/1996 | Chen et al. | |
| 5,582,170 A | 12/1996 | Soller | |
| 5,603,820 A | 2/1997 | Malinski et al. | |
| 5,930,771 A * | 7/1999 | Stapp | G06Q 10/087 705/26.5 |
| 6,210,326 B1 | 4/2001 | Ehwald | |
| 6,234,973 B1 | 5/2001 | Meador et al. | |
| 6,268,161 B1 | 7/2001 | Han et al. | |
| 6,280,604 B1 | 8/2001 | Allen et al. | |
| 6,287,452 B1 | 9/2001 | Allen et al. | |
| 6,442,413 B1 | 8/2002 | Silver | |
| 6,475,161 B2 | 11/2002 | Teicher et al. | |
| 6,514,689 B2 | 2/2003 | Han et al. | |
| 6,529,801 B1 | 3/2003 | Rosenblum | |

(Continued)

FOREIGN PATENT DOCUMENTS

| | | | |
|---|---|---|---|
| WO | WO 03/048789 A2 | 6/2003 | |
| WO | WO 2006/091123 A1 | 8/2006 | |
| WO | WO 2006136350 A1 * | 12/2006 | ........... G06Q 10/087 |

OTHER PUBLICATIONS

Avagyan et al.; "New Diagnostic Methods in Acupuncture"; ICMART '99 International Medical Acupuncture Symposium, Riga; May 21-23, 1999; p. 7.

(Continued)

*Primary Examiner* — Michael Tomaszewski
(74) *Attorney, Agent, or Firm* — Daniel J. Honz; Advent, LLP

(57) ABSTRACT

Various embodiments disclosed herein include systems, methods, and devices for automated delivery of medical services and products. In certain embodiments, the systems and/or methods are at least partially controlled by a computer.

33 Claims, 6 Drawing Sheets

(56) References Cited

U.S. PATENT DOCUMENTS

| | | | |
|---|---|---|---|
| 6,546,268 B1 | 4/2003 | Ishikawa et al. | |
| 6,697,704 B2 | 2/2004 | Rosenblum | |
| 6,764,446 B2 | 7/2004 | Wolinsky et al. | |
| 6,766,218 B2 | 7/2004 | Rosenblum | |
| 6,818,356 B1 | 11/2004 | Bates | |
| 6,823,717 B2 | 11/2004 | Porter et al. | |
| 6,892,941 B2 | 5/2005 | Rosenblum | |
| 6,965,791 B1 | 11/2005 | Hitchcock et al. | |
| 6,994,934 B2 | 2/2006 | Stanish et al. | |
| 7,006,893 B2 | 2/2006 | Hart et al. | |
| 7,144,655 B2 | 12/2006 | Jenson et al. | |
| 7,162,289 B2 | 1/2007 | Shah et al. | |
| 7,168,294 B2 | 1/2007 | Porter et al. | |
| 7,180,471 B2 | 2/2007 | Boucher | |
| 7,194,801 B2 | 3/2007 | Jenson et al. | |
| 7,205,701 B2 | 4/2007 | Liu et al. | |
| 7,206,605 B2 | 4/2007 | Hattori | |
| 7,215,887 B2 | 5/2007 | Ternullo et al. | |
| 7,218,900 B2 | 5/2007 | Suzuki | |
| 7,227,956 B1 | 6/2007 | Onishi | |
| 7,236,595 B1 | 6/2007 | Bean et al. | |
| 7,238,628 B2 | 7/2007 | Demaray et al. | |
| 7,245,894 B2 | 7/2007 | Sekiguchi et al. | |
| 7,245,956 B2 | 7/2007 | Matthews et al. | |
| RE39,785 E | 8/2007 | Fuse | |
| 7,254,160 B2 | 8/2007 | Kawamoto et al. | |
| 7,257,327 B2 | 8/2007 | Small | |
| 7,260,155 B2 | 8/2007 | Stonick et al. | |
| 7,260,402 B1 | 8/2007 | Ahmed | |
| 7,260,764 B2 | 8/2007 | Chen | |
| 7,260,768 B1 | 8/2007 | Matsumoto et al. | |
| 7,272,431 B2 | 9/2007 | McGrath | |
| 7,291,503 B2 | 11/2007 | Swager | |
| 7,340,293 B2 | 3/2008 | McQuilkin | |
| 7,444,203 B2 | 10/2008 | Rosenblum | |
| 7,469,820 B2 | 12/2008 | Rosenblum | |
| 7,471,993 B2 | 12/2008 | Rosenblum | |
| 7,774,097 B2 | 8/2010 | Rosenblum | |
| 8,033,424 B2 | 10/2011 | Rosenblum | |
| 9,043,217 B2* | 5/2015 | Cashman | E04H 3/08 705/2 |
| 9,463,412 B2* | 10/2016 | Akdogan | G07F 9/026 |
| 2002/0062175 A1* | 5/2002 | Lion | G06F 19/3462 700/237 |
| 2003/0050731 A1 | 3/2003 | Rosenblum | |
| 2003/0088332 A1 | 5/2003 | Rosenblum | |
| 2003/0093181 A1 | 5/2003 | Rosenblum | |
| 2003/0216831 A1 | 11/2003 | Hart et al. | |
| 2004/0123667 A1 | 7/2004 | McGrath | |
| 2004/0133083 A1 | 7/2004 | Comaniciu et al. | |
| 2004/0138924 A1 | 7/2004 | Pristine | |
| 2004/0164146 A1 | 8/2004 | Rosenblum | |
| 2004/0215369 A1 | 10/2004 | Rosenblum | |
| 2005/0049746 A1 | 3/2005 | Rosenblum | |
| 2006/0058694 A1 | 3/2006 | Clark et al. | |
| 2006/0060646 A1* | 3/2006 | Lee | G06Q 20/04 235/379 |
| 2006/0190419 A1 | 8/2006 | Bunn et al. | |
| 2006/0212085 A1 | 9/2006 | Fischell et al. | |
| 2006/0280307 A1 | 12/2006 | Ikushima et al. | |
| 2006/0294108 A1 | 12/2006 | Adelson et al. | |
| 2007/0008112 A1* | 1/2007 | Covannon | A61J 3/007 340/539.12 |
| 2007/0023444 A1 | 2/2007 | Holloway et al. | |
| 2007/0043469 A1 | 2/2007 | Draper | |
| 2007/0088713 A1 | 4/2007 | Baxter et al. | |
| 2007/0106129 A1 | 5/2007 | Srivathsa et al. | |
| 2007/0208454 A1 | 9/2007 | Forrester et al. | |
| 2007/0293982 A1 | 12/2007 | Rosenblum | |
| 2008/0039698 A1 | 2/2008 | Burton | |
| 2008/0045832 A1 | 2/2008 | McGrath | |
| 2008/0077440 A1* | 3/2008 | Doron | A61B 5/076 705/2 |
| 2009/0048712 A1 | 2/2009 | Rosenblum | |
| 2009/0125324 A1 | 5/2009 | Keravich et al. | |
| 2009/0240528 A1 | 9/2009 | Bluth | |
| 2009/0281657 A1* | 11/2009 | Gak | A61J 7/0481 700/242 |
| 2010/0049095 A1 | 2/2010 | Bunn et al. | |
| 2010/0174533 A1 | 7/2010 | Pakhomov | |
| 2010/0250385 A1 | 9/2010 | Lempel et al. | |
| 2010/0280899 A1 | 11/2010 | Smith et al. | |
| 2010/0324728 A1 | 12/2010 | Rosenblum | |
| 2011/0079648 A1 | 4/2011 | Pourfallah | |
| 2011/0082708 A1 | 4/2011 | Pourfallah | |
| 2011/0251850 A1 | 10/2011 | Stephens | |
| 2012/0068846 A1 | 3/2012 | Dalzell et al. | |
| 2012/0089249 A1 | 4/2012 | Rosenblum | |
| 2012/0179012 A1 | 7/2012 | Saffarian | |
| 2012/0253837 A1* | 10/2012 | Cashman | E04H 1/1205 705/2 |
| 2012/0303388 A1 | 11/2012 | Vishnubhatla et al. | |
| 2013/0173287 A1* | 7/2013 | Cashman | E04H 3/08 705/2 |
| 2013/0238119 A1 | 9/2013 | Simmons et al. | |
| 2014/0156065 A1 | 6/2014 | Melby et al. | |
| 2014/0278510 A1 | 9/2014 | McLean et al. | |
| 2015/0127145 A1 | 5/2015 | Kim | |

OTHER PUBLICATIONS

Gao et al.; "Wireless Medical Sensor Networks in Emergency Response: Implementation and Pilot Results"; IEEE; 2008; pp. 187-192; IEEE.

Harland et al.; "Electric potential probes—new directions in the remote sensing of the human body"; Measurement Science and Technology; 2002; pp. 163-169; vol. 13; IOP Publishing Ltd.

Harland et al.; "High resolution ambulatory electrocardiographic monitoring using wrist-mounted electric potential sensors"; Measurement Science and Technology; 2003; pp. 923-928; vol. 14; IOP Publishing Ltd.

Infrared Cameras, Inc.; product specification sheet; bearing a date of 2008; one page; located at www.infraredcamerasinc.com; Infrared Cameras Inc.

Lumidigm; Lumidigm Venus Series Multispectral Fingerprint Sensors; PDF created on Feb. 15, 2012; 2 pages; located at www.lumidigm.com.

Pollock et al.; "OSCAR-MDA an Artificially Intelligent Advisor for EmergencyRoom Medicine"; printed on Oct. 18, 2011; 5 pages.

Prance et al.; "Adaptive Electric Potential Sensors for smart signal acquisition and processing"; Journal of Physics: Conference Series; 2007; 012025; pp. 1-5; vol. 76; IOP Publishing Ltd.

Samhsa Opioid Overdose Prevention Toolkit: Information for Prescribers. HHS Publication No. (SMA) 13-4742; Rockville, MD 2013; available online at: http://store.samhsa.gov/shin/content//SMA13-4742/Toolkit_Prescribers.pdf; bearing a date of 2013; 12 pages.

Shaltis et al.; "Novel Design for a Wearable, Rapidly Deployable, Wireless Noninvasive Triage Sensor"; Proceedings of the 2005 IEEE; Engineering in Medicine and Biology 27th Annual Conference; Shanghai, China, Sep. 1-4, 2005; pp. 3567-3570; IEEE.

Shi et al.; "MSMiner—a developing platform for OLAP"; Decision Support Systems; bearing a date of 2007; pp. 2016-2028; vol. 42; Elsevier B.V.

Tu et al.; "A Novel Electrochemical Microsensor for Nitric Oxide Based on Electropolymerized Film of o-Aminobenzaldehyde-ethylene-diamine Nickel"; Electroanalysis; 1999; pp. 70-74; vol. 11, No. 1; Wiley-VCH Verlag GmbH.

PCT International Search Report; International App. No. PCT/US2014/064848; dated Feb. 24, 2015; pp. 1-3.

European Patent Office; Supplementary European Search Report; App. No. EP 14862648; dated May 15, 2017; pp. 1-10.

* cited by examiner

DEVICES, SYSTEMS, AND METHODS FOR AUTOMATED MEDICAL PRODUCT OR SERVICE DELIVERY

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None.

RELATED APPLICATIONS

U.S. patent application Ser. No. 14/079,778, entitled DEVICES, SYSTEMS, AND METHODS FOR AUTOMATED MEDICAL PRODUCT OR SERVICE DELIVERY, naming RODERICK A. HYDE, MURIEL Y. ISHIKAWA, JORDIN T. KARE, GARY L. MCKNIGHT AND ROBERT C. PETROSKI as inventors, filed 14 Nov. 2013, is related to the present application.

U.S. patent application Ser. No. 14/079,823, entitled DEVICES, SYSTEMS, AND METHODS FOR AUTOMATED MEDICAL PRODUCT OR SERVICE DELIVERY, naming RODERICK A. HYDE, MURIEL Y. ISHIKAWA, JORDIN T. KARE, GARY L. MCKNIGHT AND ROBERT C. PETROSKI as inventors, filed 14 Nov. 2013, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

Described herein for various embodiments include systems, methods, and devices for automated delivery of medical products or services. In certain embodiments, the systems and/or methods are at least partially controlled by a computer.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
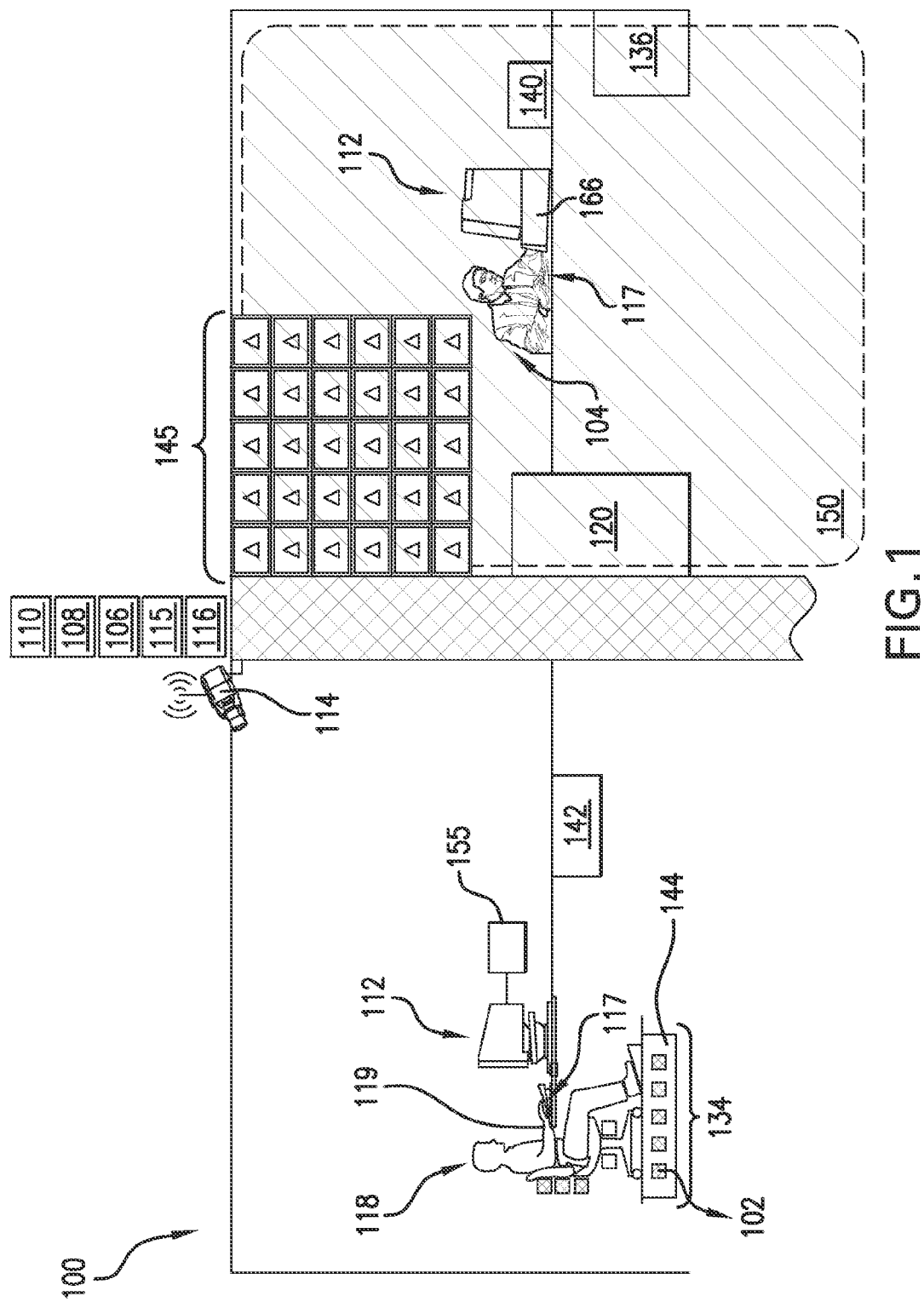
FIG. 1 illustrates a partial view of an embodiment disclosed herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In an embodiment, at least one of the methods, devices, computer systems, or computer program products disclosed herein is utilized for automated delivery of medical services or products to a subject in a healthcare setting. In an embodiment, at least one of the methods, devices, computer systems, or computer program products disclosed herein is utilized for automated delivery of medical services or products to a subject in a non-healthcare setting. In an embodiment, at least one of the methods, devices, computer systems, or computer program products disclosed herein is utilized for automated delivery of medical services or products to a subject in a kiosk located, for example, in an office; school; pharmacy; retail store; drug store; airport; church, temple, synagogue or other place of worship; hospital; nursing home or other long-term care setting; childcare facility; adult care facility; government agency; or other location. In an embodiment, at any of these locations, the subject does not directly interact with a person, but instead may interact with a computerized device for assistance. In an embodiment, the kiosk is part of a network of kiosks. In an embodiment, each kiosk in the network of kiosks is located at a separate and distinct location. In an embodiment, multiple kiosks in the network are located in close proximity (e.g., multiple kiosks in an airport, school, etc.). In an embodiment, at least one kiosk in the network includes a GPS locator to identify the location of the subject seeking the medical product or service.

In an embodiment, the methods, devices, computer program products, or computer systems disclosed herein assist in the assessment (e.g., diagnosis, temporary stabilization, determination of trauma, etc.) of a subject based on evaluated criteria (EC) and using the EC of the subject to assign a Health Status Indicator (HSI), which indicates if medical services or products may be delivered, and if so, which ones.

In an embodiment, the HSI of subjects is updated in real time with one or more of temporal, spatial, or subject-specific data. The data may be entered by a user (e.g., the subject him/herself or a healthcare provider), or by one or more sensors or other detectable indicators or tests.

In an embodiment, a request for a particular medical service or product is made by the subject or by a healthcare provider on behalf of the subject. For example, a subject may request pain relievers, antibiotics, bandages, anti-diuretics, nutraceutical, stool softeners, feminine hygiene products, cold compresses or heating pads, x-rays, pregnancy test, HIV test, cholesterol or blood glucose test, urinalysis, MRSA test, flu test, bird flu test, hearing test, eye exam, body mass index test, glucose strips, glucose finger sticks, a glucose monitor, heart monitor, etc.

In an embodiment, visual inspection by an automated computing device, or directly by a healthcare worker (e.g., via Skype, video phone, or other similar electronic interaction) is provided by a screen at the kiosk. In this way, skin tone or color, hair tone or color, pallor, bruises, lacerations, rashes, etc. and overall condition can be assessed if needed in order to satisfy the threshold to receive the medical product or service being sought by or for the subject.

In an embodiment, audio inspection by an automated computing device, or directly by a healthcare worker (e.g., via telephone, voicemail, or other similar electronic audio interaction) is provided by a microphone or other input/output device operably coupled to the computing device that interacts with the kiosk and/or network of kiosks. In this way, coughing, heartbeat, voice, or overall condition can be assessed if needed in order to satisfy the threshold to receive the medical product or service being sought by or for the subject.

In an embodiment, the request for a particular medical service or product has been previously made by the subject at a healthcare facility, where the subject obtained a coded voucher that can be scanned or manually entered by the subject or for the subject (e.g., if the subject is not a human subject, or not an adult human subject, or not capable of engaging with the kiosk him/herself).

In an embodiment the subject pre-orders and/or pre-pays for the medical service or product prior to engaging with the automated kiosk or other remote system. In an embodiment, the voucher provides for a single dispensing of the medical service (e.g., assessment or test, such as pregnancy test or HIV test, sexually transmitted disease test, malaria test, etc.) or product. In an embodiment, the voucher provides for a series or regular schedule of dispensing of the service or product (e.g., $3^{rd}$ day of each month). In an embodiment, the voucher has an expiration date or a particular time window during which the medical service or product must be obtained or the voucher terminates and is no longer able to be used. In an embodiment, the voucher includes either a paper voucher or an electronic voucher (e.g., a voucher that can be displayed on a smartphone, laptop, notebook, or other electronic device or by electronic file such as with a flash drive). In an embodiment, the voucher must be presented at a specific kiosk location in order for it to be valid. In an embodiment, the voucher may be presented at any kiosk location. In an embodiment, the voucher includes information that can be scanned, for example, by bar code, text recognition, Quick Response (QR) code, RFID, magnetic strip, keyable code sequence (numeric, alphabet, alpha-numeric, byte/binary, etc.), UPC bar code, light patterns, reflective patterns, etc. or other detectable identification. In an embodiment, the voucher contains encrypted electronic information specific to the subject, such as identifying information or information related to the prescription, payment, schedule of payment or dispensing of service or product.

In an embodiment, a subject must satisfy a verification threshold prior to receiving the requested medical product or service. In an embodiment, the verification threshold is pre-determined, and may be customized to the subject or the product or service being sought. For example, as described herein, for controlled substances, a necessarily high level of verification by the subject can be required, whereas for a bandage, a low level of verification by the subject can be required. In an embodiment, as described herein the verification threshold is satisfied by a pre-determined verification process, including, for example, identification (e.g., driver's license number, social security number, etc.), optionally a prescription (e.g., a voucher or pre-approval by a healthcare worker) or optionally insurance information or insurance approval, and optionally an assessment of the subject's electronic health record and/or queries regarding past use of the medical product or service, allergies, or other health conditions, etc. may be needed to satisfy the verification threshold. In an embodiment, the subject is seeking a medical product or service that has been pre-paid. In an embodiment, the verification threshold is not satisfied and instead the subject is denied the medical product or service being sought. In an embodiment, the subject may be referred to a healthcare facility or worker for further verification related to the medical product or service being sought. In an embodiment, the healthcare worker or facility is accessible by way of the kiosk itself. In an embodiment, the healthcare worker or facility is not accessible by way of the kiosk and in certain instances a map or other location information is provided to the subject in order to continue the process elsewhere. In an embodiment, the kiosk accesses all records for the subject via the network and if the subject has exceeded the approved level or number of medical products or services being sought, the subject is denied and the verification threshold is not satisfied. In this case, the entire network may be flagged to prevent the subject from using another kiosk in the network to seek a product or service.

In an embodiment, at the time the input information is provided to the system, if a pre-approval prescription is being sought, the prescription can be edited or deleted, for example if the subject is seeking a generic pharmaceutical rather than the name-brand pharmaceutical prescribed by the doctor, or if the subject is seeking an equivalent pharmaceutical drug that is approved by the subject's insurance. The subject inputs information into the input/output device that requests that the prescription be edited. The system includes circuitry configured for specific modifications of the prescription without further approval, as was previously entered by a healthcare worker, and grants the modification if it falls within the range specified for approval by the healthcare worker. If the requested modification falls outside the range specified for approval by the healthcare worker, then the request to modify the prescription is denied. The subject can continue with the original pre-approved prescription, or seek further engagement with the kiosk system in order to seek approval following the first round denial. If, upon further input of information into the system and optionally consultation with an automated computerized response system or human healthcare worker, the request to modify the prescription is satisfied, then the prescription is noted as modified and such information is shared with the kiosk system. The originally pre-approved prescription is then noted as deleted or refused by the subject.

In an embodiment, all input information and output information related to the engagement of the subject with the kiosk is shared with the network to which this particular kiosk is a member, if a network exists. In an embodiment, all information regarding any particular subject is updated in real time such that the subject cannot attempt to redeem more than one voucher or pre-approved prescription, or cannot attempt to seek outright a medical product or service at more than one kiosk. Thus, the updated information regarding the subject prevents abuse of the system by prohibiting the subject from seeking the same thing twice within a specified time frame. As indicated herein elsewhere, the subject may seek a medical product or service on a schedule, as approved by a healthcare worker, which provides for automatic renewal of the eligibility to receive the medical product or service at a specific time, after a specified time period, or at a continuing time point. In an embodiment, the output includes dispensing of the requested medical product or service.

In an embodiment, the subject or someone acting on behalf of the subject (e.g., if the subject is a minor, or non-human animal) is required to sign a signature box as part of the kiosk system input on the input/output device (for example, with a stylus or finger). Alternatively, a fingerprint may be provided instead of a signature for receipt of the product or service.

In an embodiment, the system alerts the subject if the subject is seeking a medical product or service that may cause adverse reactions with an item in the subject's personal medical history records (e.g., other medications, allergies, etc.). In an embodiment, this alert prevents the subject from receiving the medical product or service being sought and requires further interaction with the kiosk to modify the request, or interaction with a healthcare worker (e.g., either by telephone, videophone, email, chat, etc.) at the kiosk, or the subject is instructed to seek medical attention and the request is outright denied.

In an embodiment, input information related to the subject seeking a medical product or service is shared with one or more of a vendor, social media, corporate sponsor, advertising partner, corporate partner, or other third party. In an embodiment, the subject is notified that such sharing may be optional. In an embodiment, input information related to the subject is anonymized prior to sharing. In an embodiment, input information related to the subject seeking a medical product or service is shared with health databases, such as the CDC, state, local, or federal agencies. In an embodiment, the subject is notified that in order to proceed to seek the medical product or service being sought, it is necessary to share certain or all information related to that subject.

In an embodiment, a verification code not provided with the voucher but also given to the subject or subject's guardian (e.g., by text to a cell phone) is required for added security when obtaining the medical service or product at the kiosk by using a voucher.

In an embodiment, the subject is able to check (e.g., by electronic access through the internet or another network) that a particular kiosk has the subject's particular medical service or product available.

In an embodiment, the methods, devices, computer systems, or computer program products save healthcare facilities time, money, and reduce errors by increasing efficiency and collecting and presenting accurate information about each subject receiving automated medical services or products. Likewise, the methods, devices, computer systems, or computer program products provide benefits to subjects, including but not limited to, customized attention, time savings, money savings, insurance compliance (including governmental compliance), reduction of errors, easier documentation (e.g., automatic recording of dispensing of a drug), inventory control, controlled-substance control (for example by networking with the Drug Enforcement Agency), expiration management of any products that have an expiration date, and faster treatment. Thus, various embodiments disclosed herein assist healthcare facilities, particularly emergency departments, reduce the overload of subjects who are able to receive adequate medical attention without having to go to the emergency room. Further, the high level of data collection from the subject at the kiosk or other remote location results in fewer re-billing events for payment of services due to inaccurate information received, or mistakes made on intake of the subject to a healthcare facility.

In an embodiment, the methods, devices, computer systems, or computer program products also access any electronic health records that can include, among other things, the subject's past medical problems and/or treatments as well as possible identifying information. In an embodiment, the subject can request that his/her electronic health records be transferred to the kiosk, for example by uploading them to the kiosk, by way of scanning them in, by inserting via flash drive into the kiosk device, or remotely by electronic transfer by way of the internet or other secure network access.

In an embodiment, where the medical service or product is an unusual one, the subject may pre-order the product or service, or get pre-authorization (e.g., by way of voucher as described herein for other embodiments) and the kiosk will then stock the product or service not usually stocked at the particular kiosk. In an embodiment, the stocking and order may be electronically or automatically controlled, or may be manually entered into the system. In an embodiment, the kiosk is part of a network utilizes standard inventory control principles adapted to the various embodiments disclosed herein, for example, by utilizing reordering points that detect a quantity or date that indicates it is time to re-order a particular product or service. For example, each product or service (if not located in a locked dropbox, as described herein) may be located in a cartridge that allows for the product or service to be easily delivered. In an embodiment, the re-stocking of various kiosks is done by way of a central location, a regional location, or an individual location. Thus, the worker or automatic re-stocking occurs in a manner similar to re-stocking a vending machine, with additional levels of verification of identity of each product or service being stocked in the kiosk.

In an embodiment, the kiosk includes lockers (e.g., heavy metal locked boxes or safes) that are configured to be opened only by way of the voucher form the subject has obtained by the prescription writing healthcare provider and optionally by added security features such as providing subject identification (e.g., fingerprint, driver's license number, debit card, date of birth, social security number, subject-specific health record number, insurance card number, iris scan, passport number, credit card, Flexible Saving Account card, Health Saving Account card, Health Reimbursement Account card, etc.) or optionally by a verification code obtained from the healthcare provider but not necessarily located on the voucher (e.g., a text or email or separate code obtained by the subject). In an embodiment, the coded locks include a termination time so that the voucher must be presented to open the locked box during a specific time period or the medical service or product can no longer be obtained by the subject. In an embodiment, the locked boxes are configured to be opened by a key, which is provided to the subject by the healthcare provider or in another manner. In an embodiment, the key or code utilized to open the locked drop box is patient specific or service/product specific. In an embodiment, a reading and/or imaging apparatus is utilized for reading/imaging a credit card or debit card, social security card, insurance card, voucher, etc. and the image or other electronic information is communicated through the network for use in evaluating the identity, payment, insurance coverage, etc. of the subject.

In an embodiment, each engagement with any aspect of the kiosk, including the locked boxes, is recorded (e.g., by camera and/or electronic gate). For example, the locked drop boxes may record when the box is opened and filled, as well as opened and emptied. In an embodiment, a printed receipt of this activity is created either electronically or printed, to the worker filling the locked box, or to the subject receiving the product or service. In an embodiment, the locked boxes include codes that change after a designated time period, so that the subject must receive an updated code in order for the voucher to be valid.

In an embodiment, the system includes a real-time data collection and integration with the kiosk system for health information, payment information, identification, etc.

In an embodiment, payment for the medical service or product is handled directly by the kiosk, or the kiosk system. In an embodiment, payment is handled by the supplier of the product or service (e.g., by the pharmacy or pharmaceutical warehouse that supplies the kiosk). In an embodiment, the kiosk is configured to submit claims to a subject's insurance company. In an embodiment, the kiosk is configured to send bills to the subject prior to, during, or subsequent to the subject receiving the medical product or service, such as, for example, with a subject that is set up to receive regularly scheduled pick ups, or if the subject is able to pay electronically at another time (e.g., pre-authorization for credit card charge or other authorization, such as by an online electronic payment system may be required prior to allowing the subject to obtain the product or service prior to payment). In an embodiment, the bills are submitted to the subject electronically. In an embodiment, the bills are submitted to the subject by paper billing. In an embodiment, the insurance reconciliation and payment from the subject is all done electronically, prior to the subject receiving the medical service or product from the kiosk. In an embodiment, a method for obtaining payment from a subject or user (e.g. if the subject is a minor or non-human), for example by credit card, debit card, blue tooth payment, smart card, cash card, cash bill or check reader, electronic online payment, or other, as described herein.

In an embodiment, the kiosk is able to determine the coverage of the subject's insurance, and direct the subject to medical services or products that are covered under the subject's plan and optionally away from those that are not. For example, the kiosk may provide a list of "Insurance authorized" products or services, and "Insurance not authorized" products or services, with the respective costs to the subject also visible. In this way, the subject may elect to have a product or service covered by the insurance plan, or not, and pay the corresponding costs associated with that decision.

In an embodiment, a weight may be necessary as part of the evaluation of the subject, for example, in a situation where the subject is a pediatric or young patient. The dosage of a product or service may depend on the weight or age of the subject in certain instances, such that either the weight is accessed by way of health records, prior input, or subject input at present, or a scale (e.g., embedded within a chair or the floor or a counter top) is present at the kiosk and a current weight of the subject may be obtained. In the event of the subject being a baby or very young patient, the kiosk may query whether a car seat or other baby holding device is present on the scale, and instruct the user to zero balance the scale with the baby carrier alone (without the subject) and then place the subject into the baby carrier, in order to obtain an accurate reading of the subject's weight.

In an embodiment, the kiosk alerts the subject if a suggested product or service (or one requested by the subject) is not currently available at this particularly location, and optionally provide the map or directions for availability of the nearest kiosk that does have that particular product or service. In an embodiment, the kiosk recommends an alternative product or service that is located at this particular kiosk location.

In an embodiment, a subject has received a voucher or recommendation for a particular product or service, but changes his/her mind. In the case of a voucher, for example, the subject may request that an alternative product or service be provided instead of the one(s) listed on the voucher (e.g., generic version of a trademarked drug), and the kiosk will determine whether or not this is possible, based, for example, on the subject's health history or queries, availability at this particular kiosk location, and/or other Evaluated Criteria. In an embodiment, the kiosk is able to grant the request to modify the voucher, and the original voucher is voided or held inactive by the kiosk network. In an embodiment, the kiosk is not able to grant the request to modify the voucher. In an embodiment, if the voucher is modified, a second level of identity confirmation and/or evaluation may occur. For example, the kiosk will confirm with the subject that the subject is not allergic to the product/service, or is not taking any pharmaceuticals that may have adverse reactions with the modified voucher request.

In an embodiment, the subject's request for a particular medical service or product is validated, for example, by checking with electronic health records or pharmacy databases, as well as with the Drug Enforcement Agency for information related to the subject, and whether the subject is authorized to receive the requested medical service or product. In an embodiment where the subject has a voucher from a healthcare worker prescribing the medical product or service, the prescription may be validated based on terms of the prescription and the subject's prior use of the kiosk (e.g., # of pills per day, time since last pill, # left on prescription, etc.) on a system-wide level.

In an embodiment, a roving worker transfers the medical product or service to the locked dropboxes at a scheduled time (e.g., once a day) or as needed. In an embodiment, one or more lock boxes keeps stock at least one particular product or service obtainable by a subject.

In an embodiment, the subject includes a human. In an embodiment, the subject includes a healthcare worker. In an embodiment, the computer systems, devices, methods, computer program products determine whether a healthcare worker is eligible to directly or remotely program the automated system to deliver the medical service or product to the subject, access a particular healthcare database, or perform a certain task (e.g., diagnosis, run tests, dispense pharmaceutical drugs or implements). In an embodiment, the subject includes a healthcare patient. In an embodiment, the subject is a fetus. In an embodiment, the subject is a non-human animal. In an embodiment, the subject is a mammal, amphibian, fish, bird, or reptile. In an embodiment, the subject is a baby or child. In an embodiment subject is a geriatric. In an embodiment, the subject is a non-adult. In an embodiment, the subject is a cow, horse, dog, cat, or other domesticated animal.

In an embodiment, the systems, devices, methods, and computer program products described herein do not diagnose a subject. In an embodiment, the systems, devices, methods and computer program products described herein do not treat a subject, but rather instruct the subject to seek immediate medical attention such as, for example, at the closest emergency room, urgent care, or similar hospital facility. In an embodiment, the systems, devices, methods, and computer program products described herein instruct the subject to seek insurance approval prior to continuing with the process of automated delivery of medical services or products. In an embodiment, the systems, devices, methods, and computer program products described herein instruct the subject to submit payment (e.g., electronically via credit card or bank account, etc.) prior to continuing with the process of automated delivery of medical services or products.

In an embodiment, the subject receives pharmaceutical drugs either previously prescribed by a healthcare worker (e.g., doctor, nurse, mid-wife, nurse practitioner, etc.) or prescribed by way of the kiosk itself (e.g., by way of sensed information or information provided by the subject, information provided by a healthcare worker, or a health record (e.g., an electronic health record). In an embodiment, the subject must provide identification in order to receive the pharmaceutical drugs from the kiosk. In an embodiment, a single dose is provided to the subject by way of the kiosk. In an embodiment, a video camera records the subject receiving and optionally taking the drug or other medical product or service (e.g., imbibing, consuming, ingesting, applying, etc. or otherwise utilized the dispensed medical product or service). Thus, in an embodiment, the kiosk includes at least one of audio or video recording (e.g., the kiosk includes a microphone, camera, keyboard, etc.) and may include instant messaging, audio or video transmission. In an embodiment, the camera includes a digital camera or webcam. In an embodiment, the kiosk accepts video or audio recording of the subject by way of the subject sending a recording of itself utilizing the medical product or service by way of mobile phone, electronic tablet, or digital camera to the kiosk.

Thus, in an embodiment the kiosk provides verification that the subject has ingested or otherwise utilized the dispensed medical product or service.

In an embodiment, the prescription drug includes a measurable indicator, such as a radio frequency identification device, such that the kiosk itself is configured to monitor the drug in the subject's body (e.g., by way of transmission/reception of signals with the drug by way of a computer system). In an embodiment, the medical product or service includes packaging that has a radio frequency identification device or radio frequency reflector that is configured to transmit a signal once the package is opened or disturbed. For example, the box that houses a glucose testing kit contains an RFID, or the bubble packaging for a particular pharmaceutical drug each contains an RF reflector so that upon utilization, the signal is transmitted to the kiosk or to a third party.

In an embodiment, a subject seeks to obtain a sub-portion of a prior prescription, and the kiosk is configured to access the subject's health records and determine that the subject is allowed to obtain the requested sub-portion of the drug, and if so, then the kiosk dispenses the requested sub-portion. If the kiosk determines that the subject is not permitted to obtain the requested sub-portion, then the kiosk may optionally be configured to either deny the subject any of the drug, the kiosk may dispense only what is permitted, if any, to the subject, or the kiosk can request further information from the subject to evaluate whether or not to dispense at least one dose of the pharmaceutical drug to the subject. In an embodiment, the further information may include queries to the subject, queries to the subject's medical record(s), or queries by way of sensors engaged with the subject.

Thus, in an embodiment, a kiosk including at least one computing device receives at least one input from a subject relating to a subject's seeking a portion of a prescribed medical product or service and, utilizing circuitry of the computing device, compares the input from the subject with one or more verification datasets, and the computing device generates a verification value based on the comparison. For example, the verification dataset may include information related to identification of the subject, codes (insurance codes, security codes, etc.) or prescription information. In an embodiment, the verification dataset further includes medical records or a medical record database of the subject, including physician information (or other healthcare worker information) health care profile, state of health, etc. Once the system has satisfied a verification threshold, dispensation of whole or part of the portion sought by the subject occurs. If the verification threshold is not met, the request by the subject is denied. In an embodiment, the subject is also referred to seek additional authorization, such as from a health care worker, pharmacy, or insurance company. In an embodiment, the subject is instructed to seek additional medical attention. The portion sought by the subject may include at least one daily aliquot, one weekly aliquot, one monthly aliquot, or any value therebetween, depending on the particular medical product or service being sought (e.g., liquid, pill form, device form, etc.), and the portion sought by the subject may include any amount less than the full prescription amount usually dispensed (e.g., as a one time prescription such as for antibiotics, or as an on-going prescription such as for birth control pills).

In an embodiment, the computing device of the kiosk further accesses one or more healthcare providers for confirmation of the prescription or portion thereof.

In an embodiment a system includes a medical record database in communication with the kiosk, that communicates with the kiosk an output indicative of the satisfaction or denial of a medical record threshold upon inquiry or input from a subject for a medical product or service (e.g., a portion of a prescribed medical product or service). Thus, in an embodiment, the kiosk communicates to the subject's medical records, and the medical record database communicates with the kiosk. In an embodiment, the medical record database may include one or more of a subject's prescription information, pharmacy information, health care worker information, or health insurance information. In an embodiment, the computing device communicating with the kiosk includes generating an output indicative of the satisfaction or denial of a medical record threshold (e.g., medical record dataset differs from the verification dataset in that the verification dataset may include the medical record dataset as well as other identifying information). In an embodiment, the medical record threshold satisfaction or denial is determined by at least one of presence of an available prescription for which the subject is seeking dispensation, approval of a new prescription for the subject for which the subject is seeking dispensation, means for contacting a health care worker for approval (e.g., transmitting a signal from the medical database to a physician for approval) for example, for a chronic condition or on-going health issue related to the medical product or service sought, or approval by a health insurance company for a prescription for the subject. In an embodiment, the system communicates the output indicative of the satisfaction or denial of a medical record threshold with at least one of a health care worker, pharmacy, or health insurance company. In an embodiment, the computing device associated with the medical record database is configured to receive at least one input from the kiosk indicative of the dispensation of all or part of the prescription (or portion thereof) sought by the subject. In an embodiment, the dispensation includes a quantity or amount of the prescription dispensed. In an embodiment, the dispensation is recorded in the subject's medical records and/or transmitted to a third party (e.g., insurance company, health care worker, pharmacy, etc.).

In an embodiment the medical services or products include prescription products or services. In an embodiment, the medical services or products include non-prescription products or services. In an embodiment, the system has a specific user identification (e.g., fingerprint, social security number, random subject identifier, retinal scan, etc.) to identify the subject. In an embodiment, a security breach identification service operates to alert the system when the kiosk or other remote facility has had an attempted disabling or other destruction or assault. In an embodiment, product identification (e.g., RFID tag) alerts the system if it has been obtained by way of breaking or disabling the kiosk. In this regard, a "check out" procedure may be implemented as part of the process of the subject requesting the medical product or service, and in order to control for inventory and security. If the "check out" procedure is breached in any way, the system shuts down and the security alert is triggered. In an embodiment, each engagement of the kiosk system is registered or recorded (e.g., by camera) and may be logged within the system. In an embodiment, automatic tracking of inventory includes automatically ordering more of a particular product when that product has run low (e.g., decreased past a certain threshold that triggers an automatic system alert to order more), and in an embodiment, any drug or other product recalls are automatically transferred within the system through the network such that no additional dispensing of the recalled product occurs, and optionally the subjects having already received the recalled product are notified (e.g., by text to their cell phone, by email, by written mail notice, by telephone call, etc.).

In an embodiment, non-prescription medical services or products can be purchased by credit card/debit card/smart phone/wired money transaction/cash/electronic money transaction, or other means. For example, the kiosk may contain containers or compartments for dispensing particular implements, such as eye glasses, canes, walkers, braces, and the like, that may be dispensed for example, by a tube or other single-action mechanism. In an embodiment, multiple requests by the subject are satisfied in one single transaction. In an embodiment, the subject is required to submit separate requests for each product or service requested.

In an embodiment, a voice recognition or facial recognition system is utilized for verification of the subject's identity, request, or receipt of the product or service requested.

In an embodiment, the system includes a network, such as an intranet or the Internet, or other local and wide area networks. As described herein, a host system may network to one or more remote kiosks or other remote locations or facilities that may be in different geographical areas, such as different parts of a city, different cities, different states, different countries, etc.

In an embodiment, the subject is provided with one or more options for obtaining a medical service or product. For example, if the subject reports having a headache and requests non-prescription pain reliever, the kiosk or other interactive remote dispensing system may ask if the subject has an allergy or prefers one pain reliever over another, for example, by listing aspirin, acetaminophen, or ibuprofen.

In an embodiment, a particular subject undergoes assessment with one or more sensors. For example, in an embodiment, the subject is assessed with one or more first sensors that then activates one or more second sensors, depending on the conditions sensed and criticality of the subject based on the first sensing (and optionally, consideration of information included in a subject's health record(s)) a first sensor initiates a system (e.g., a subject passes by it or enters the facility), or self-reporting of characteristics (e.g., symptoms) by the subject. In an embodiment, the subject undergoes assessment based on a decision tree originating with the first sensor and/or self-reporting of characteristics (e.g., symptoms) by the subject. (See for example, Shi et al., Science Direct pp. 2016-2028, Vol. 42 (2007); U.S. Patent App. Pub. No. 2010/0049095, the content of each is incorporated herein by reference.) For example, nonphysiologic and physiologic sensing can be performed by one or more sensors of the system alone or in conjunction with biological assays, which can be performed by the system (blood glucose finger prick test, breathalyzer, DNA swab, pulse-oximeter, etc.), or self-reporting by the subject of any characteristics (e.g., symptoms) and of the subject's perceived severity or criticality of such characteristics (e.g., symptoms) (e.g., battery of questions or a figure of a human or other model subject for reporting the location of pain or other trouble) in order to generate one or more Evaluated Criteria for the subject. In an embodiment, the subject is unaware of the assessment with one or more sensors. In an embodiment, the subject is unresponsive or unconscious. In an embodiment, the subject is given a choice as to whether to be assessed by the one or more sensors. In an embodiment, a privacy curtain or separate room space is designated for particular evaluations of the subject, or if the subject request it. In an embodiment, a curtain or other privacy screen closes automatically when the subject engages with the kiosk. In an embodiment, a subject may plug in a set of earphones or his/her own personal ear phones to hear any audible alerts or messages from the kiosk.

Next, depending on the results of the assessment (i.e., sensed conditions, biological assays, self-reported characteristics, and optionally the subject's health record(s) (e.g., electronic health record)), and the corresponding Evaluated Criteria for the subject, based on comparison with a characterization value dataset. Once the EC for the subject are generated, the subject is assigned a Health Status Indicator (HSI) value based on comparison with a health status value dataset. The health status dataset may include indications, values or statistics of various bodily measurements or results of assays or sensed parameters, including but not limited to blood pressure, heart rate, body temperature, height, weight, body mass index, pupil size, blood glucose, muscle mass, viral load, viral infection, bacterial infection, bacterial load, pregnancy status, pharmaceutical or other drug presence or level, tumor presence or status, blood type, allergy status, nutrition status, and others. The health status dataset may include general population statistics, it may include statistics from a particular selected population group (e.g., based on gender, familial history, demographic, or geographic group), it may include the subject's own previously collected health records or information, or any combination thereof.

In an embodiment, sensed, assayed, or reported characteristics are compared with known values, including but not limited to a database of standardized values, or a subject's own health history values. Based on the HSI of the subject, a decision is made utilizing instructions implemented on a computing device (network, etc.) to initiate a second set of sensors, biological assays, or health queries (HQs). The second assessment can be predetermined or customized for a particular subject, depending on the needs of the healthcare facility or the needs of the subject.

For example, if it is detected or self-reported that a subject has an elevated heart rate and possible fever, the information from the subject's health record (or information from friends/relatives that are with the subject) can be considered in order to determine which immunizations the subject has or has not received. This may prompt an HQ of asking the subject if he/she has traveled anywhere recently, or been in close proximity to someone who has. This may also illicit further sensors to sense additional characteristics or the system to perform biological assays (e.g., finger prick for blood test with PCR for pathogens, etc.) and evaluate the overall condition of the subject based on the sensed conditions. If further sensors or biological assays indicate that the subject has no other symptoms, for example, this finding will determine a particular HIS and instruct the subject as to what steps to take next (e.g., seek further medical attention, take a fever-reducing medication sold over the counter or by prescription, seek rest, etc.).

In an embodiment, at least one first sensor or other components of the system is in operable communication with at least one second sensor or other component. In an embodiment, the at least one first sensor or other component is in wireless communication with at least one second sensor or other component. Various modes of wireless communication are described herein. In an embodiment, information obtained or collected regarding the subject is shared or transferred from one part of the system to another. For example, the results of an assay can be entered into the subject's medical records, or the subject's health records can direct the focus of a sensor for assessing the subject's present state of health. In this way, in an embodiment, the system represents an integrated system of multi-directional communication between one or more parties, including at least one of a subject, a healthcare worker, one or more databases, and one or more assays, sensors, or self-reporting queries. In an embodiment, assessing at least one symptom of the subject as an evaluated criteria includes in the input for receiving a medical product or service. In an embodiment, assessing includes registering at least one self-reported responses to one or more health queries. In an embodiment, as described herein.

In an embodiment, at the time the subject first engages with the kiosk, he or she can refuse to have any data collected by way of assessment (e.g., sensors, biological assays, health record (including prescription records, stored electronic monitoring data, etc.), family health history (including questioning family members), or HQs). In such a situation, for example, the subject may still provide a fingerprint, driver's license, social security number, birth date, anonymous unique identifier, or other form of identification for check-in, and optional accessing of the subject's health records, depending on the request made by the subject (e.g., to obtain part or all of a prescription drug). In an embodiment, a date and/or time stamp is registered at the time the subject engages with the kiosk or begins the assessment process. In an embodiment, the system, devices, methods, etc. are fully scalable to accommodate multiple "feeder" healthcare facilities or healthcare workers utilizing the kiosk, or multiple different delivery devices within one kiosk system or kiosk location. For example, in an embodiment there are multiple lock boxes or cartridges for delivery a product or service.

In an embodiment, the systems, devices, methods, or computer program products described herein include the ability to interact with additional information from, for example, another computer system of dataset (e.g., personal data storage, personal monitoring device or sensor network, patient tracking system (e.g., Amelior EDTracker), information system (e.g., Amelior ED), network sensors (e.g., mT Tag™ or other network sensor), implanted sensors, or user input. See for example, U.S. Patent App. Pub. Nos. 2007/0088713, and 2006/0212085, each of which is incorporated herein by reference.

In an embodiment, the sensors include at least one of an electric potential sensor, high input impedance electrometer, electromagnetic sensor, radiofrequency sensor, microwave sensor, micropower impulse radar sensor, ultrasonic sensor, imager, camera, thermal sensor, laser, infrared sensor, or audio sensor. In an embodiment, the sensor is located in at least one of the walls, floor, input/output device, door, doorway, pen, stylus, or computer system hardware. In an embodiment, the imager includes at least one of a thermal imager, light imager, or ultrasonic imager.

In an embodiment, the sensor includes at least one of an ECG, EOG, EEG, MEG, pulsometer, oximeter, pupillometer, fluid detector, biomechanical assessor, spectrophotometer retinal interrogator, respiration detector, spirometer, or implanted physiological sensor. In an embodiment, the fluid detector includes at least one microfluidic chip or device. In an embodiment, the respiration detector includes at least one of a remote imager or direct pressure sensor.

As described herein, the various components of the systems include one or more transmitter, transceiver, or receiver in order to communicate among and between components, such as for example, within the kiosk network or in certain cases, beyond the network.

In an embodiment, the systems, devices, methods, or computer program products described herein include access to the subject's health history (e.g., individual and/or family health history). In an embodiment, the systems, devices, methods, or computer program products use artificial intelligence for at least one step of the described embodiment(s) (e.g., OSCAR-MDA, CodeBlue, etc.).

In an embodiment, the systems, devices, methods, or computer program products described herein include interaction or tracking information with other datasets, for example, a public health database (e.g., CDC, NIH, state or local agency database, etc.). In an embodiment, the systems, devices, methods, or computer program products described herein access and interact with infectious disease information, bio-weapon or chemical weapon information (e.g., Homeland Security), adverse effects of drugs or equipment (e.g., for manufacture recalls), or healthcare facility statistics (e.g., infection rates, hygiene, liability, etc.). In an embodiment, a decision may be made based at least partly on information received from such a database, that the subject must be quarantined. In an embodiment, information is transferred one or more directions, including updating databases with infectious disease or other public health issues (signs of bio/chemical weapons), adverse effects to drugs or equipment (e.g., for recalls), hospital issues such as infection rates, hygiene, or liability.

In an embodiment, the HSI of the subject or HQ satisfies a threshold condition, and optionally indicates that one or more Evaluated Criteria of the subject must be monitored. For example, the subject can be monitored continuously or intermittently (e.g., at predetermined times or customized times) based on the subject or subject's condition. For example, if a particular subject is requesting a narcotic prescription, but an HQ or EC indicates that the subject already has narcotic or narcotic metabolism by-products in its body, the prescription may be denied, the subject may be assessed further (e.g., determine the precise level of narcotic or by-products in the blood), or directed to a physician or other healthcare worker.

In an embodiment, one or more sensors utilized in assessing the subject, including one or more remote non-conductive sensors, are located in one or more of furniture, wall, floor, door, doorway, reception counter, pen, computer monitor or other hardware, or computing device from which a subject is self-reporting one or more characteristics (e.g., symptoms). In an embodiment, the one or more sensors are included in an exam table, chair armrest, gurney, or other furniture.

In an embodiment, the one or more sensors include at least one of ultrasound, bioimpedance, or infrared thermometry. In an embodiment, the one or more sensors include audio sensors (e.g., cameras that are audio and/or video recorders), or eye tracking (e.g., imagers). See, for example, U.S. Patent App. Pub. Nos. 2010/0049095; 2006/0190419; 2008/0039698; or 2010/0174533, or U.S. Pat. No. 6,475,161, each of which has been incorporated herein by reference.

In an embodiment, one or more subject specific characteristics are measured, including but not limited to characteristics of the subject including at least one of height, weight, fingerprint, facial features, visible physical malformations, eye characteristic, appearance of skin, appearance of hair, appearance of nails, respiratory sounds, body temperature, blood gas level, heart rate, brain electrical activity, respiration rate, facial expression, blood chemistries, blood cell counts, platelet counts, antibody titer, calcium level, blood antigen type, tissue antigen type, evidence of a pathogen exposure, lipids levels, perception of pain level, body movement (tremors, spasms, or paralysis, etc.), gait, stiffness (e.g., muscle or joint stiffness), evidence of cognition state, dehydration, self-reported pain, self-reported malaise, self-reported injury, self-reported event, rigor, fever, self-reported light-headedness or dizziness, self-reported dry mouth, self-reported nausea, self-reported shortness of breath, self-reported thirst, weakness, self-reported sleepiness, hearing loss or problem, vision loss or problem, self-reported constipation or diarrhea, flatulence, self-reported urinary incontinence, self-reported loss of smell or problem, self-reported loss of voice or problem, self-reported loss of taste, self-reported loss of ability to walk, self-reported loss of ability to write, self-reported loss of ability of limb or digit use, or other characteristic. For example, the appearance of skin, hair, or nails can be evaluated by standard criteria, including but not limited to hair loss or change in condition, change in any birthmarks, tattoos or skin blemishes (or arise of any new birthmarks, moles, or other skin marks), body odor, change in nail condition, damage due to exposure to sun or chemicals, etc. In an embodiment the evidence of cognition state includes at least one visual or auditory cue.

In an embodiment, one or more subject specific characteristics are assessed by one or more direct or indirect sensors (e.g., remote non-conductive sensors). In an embodiment, one or more subject specific characteristics are assessed by self-reporting by the subject. For example, in an embodiment, the subject interacts with at least one input/output computing device (e.g., kiosk, tablet, desktop, laptop, handheld device, etc.) and responds to health queries (HQs) relating to his or her characteristics (e.g., symptoms) or requests. For example, in an embodiment, the subject may be presented with (in any number of different possible languages or audio/visual representations such as pictures of a body denoting points of pain or illness) HQs relating to one or more characteristics of: abdominal pain, knee pain, blood in stool, low back pain, chest pain, nasal congestion, constipation, nausea or vomiting, cough, neck pain, diarrhea, numbness or tingling in hands or feet, difficulty swallowing, pelvic pain (female or male), dizziness, eye discomfort and/or redness, shortness of breath, foot or ankle pain, shoulder pain, foot or leg swelling, sore throat, headache, urinary problems, vision problems, heart palpitations, hip pain, wheezing, joint or muscle pain, skin rash or other rash, earache, or other symptoms.

In an embodiment, the HQs asked of the subject are customized and directed based on previous answers provided or other information known about the subject (e.g., by way of the self-reporting, or by way of electronic health record, sensed information, etc.). For example, the HQs may be different based on the person's gender, health history, or response to answering a first round of specific HQs. In an embodiment, the HQs are prioritized, for example, based on symptoms or request made (e.g., request for narcotic pain reliever) with the first HQ having a heavy weight assigned due to its criticality or seriousness of symptom(s), and depending on the response to that HQ, the HQs that follow are tailored to address the concerns presented in the prior response.

For example, if a subject with a history of heart disease engages with the kiosk or other remote facility, and a first remote non-conductive sensor senses and signals that the subject has an irregular heartbeat, a second sensor quickly determines if the subject is responsive enough to answer HQs. If so, one of the first HQs for this subject could be: "How may I help you?" If the subject responds by requesting a full or partial dose of his nitroglycerine prescription, for example, the second HQ might be: "Do you have chest pain?" If the subject responds, "Yes," then another HQ could be, for example: "Rank your level of pain on a scale of 1 to 5, with 5 being greatest level of pain." Again, depending on the response, with each HQ receiving a particular numerical Evaluated Criteria value, the HQs will be adjusted specifically for the reporting subject. For example, if the subject reports a high level of pain "5," the system will determine that the subject has a high Evaluated Criteria value, and when compared with the Health Status Indicator dataset, generates a specific overall HSI value.

When one or more HSI values satisfy a threshold condition, the subject is assessed further, questioned further, or instructed to receive further medical attention at a healthcare facility. Depending on the responses by the subject, and optionally the subject's health records (e.g., accessed electronically) he/she may or may not receive his/her requested prescription. In an embodiment, the subject receives a placebo instead of the requested medical service or product.

In an embodiment, subject identification, request, payment authorization and/or insurance coverage is received by the kiosk device or system as a single data entry point by having the subject complete the step of entering information from his/her insurance card (e.g., scanning it, manually keying it in, orally reading it, etc.) or may be received by the kiosk device or system as multiple different data entry points by having the subject complete separate steps of entering information from a driver's license or social security card, a credit or debit card, and/or insurance card. If the subject has previously used a kiosk in the system, then entering this information is unnecessary, and in an embodiment, the subject is given a secure access (e.g., log in username and password) so that the subject may save time by not having to enter identifying information each time he/she uses the kiosk device or kiosk system. Thus, in an embodiment, the system includes a storage component, as described in the Figures, that stores one or more pieces of health information related to one or more of electronic health records, Evaluative Criteria, HQs (and/or answers thereto), subject-entered information, information entered by a healthcare worker, etc. Likewise, as part of the regularly scheduled medical product or service delivery described elsewhere, in an embodiment the subject does not need authorization to receive the same medical product or service, but instead merely logs in the system and requests the regularly scheduled portion of the prescription already put in place and previously authorized. Thus, a prescription voucher or evaluation is not always required for particular embodiments described herein.

In an embodiment, the subject's request is granted and the medical service or product is processed for dispensing directly at the kiosk or another location. In an embodiment, during processing, the kiosk has been pre-loaded with various commonly prescribed pharmaceutical drugs, implements, or tests. In an embodiment, the system or device includes labeling the product container or service slip, and optionally includes subject-specific information, as well as information of the contents therein. In an embodiment, the kiosk dispenses the medical product or service by scanning a code on the label or on the container. Various types of codes are described herein elsewhere.

In an embodiment, the information input from the subject is assigned varying degrees of confidence depending on the source of the information, in order to reduce conflicting information. For example, if a subject self-reports a high level of pain, but sensors detect no corresponding characteristics typical of a high level of pain (e.g., rapid heart rate, perspiration, agitation, facial expressions of discomfort, etc.), the self-reported HQ of a high level of pain may receive a lower numerical value than if the one or more sensors verify characteristics typical of a subject's being in a high level of pain.

In an embodiment, exemplary HQs include but are not limited to, "What have you tried for your condition today?" "Do you want to request a prescription drug? If yes, have you received a prescription for this drug before? If no, do you want to request a non-prescription drug?"; "Do you want to request any prescription services or implements?" "Do you smoke?"; "Do you have any allergies? If yes, are you allergic to any pharmaceutical drugs?"; "Do you have any changes in skin or hair?"; "Do you have shaking or tremors?"; "Do you have numbness anywhere in your body?": "Have you traveled lately?"; "Do you have difficulty swallowing?"; "Have you ever had a fainting spell or convulsion?"; "Do you have any lumps or bumps in your body?"; "Please indicate whether you are male or female."; "Are you pregnant?"; "Any change in appetite?"; "Are you sexually active?"; "Do you have any vomiting?"; "Do you drink alcohol?"; "List any drugs ingested in the past 24 hours, including recreational or pharmaceutical drugs."; "Have you had any medical biological assays or treatments (including surgeries) lately?"; "Rate your pain on a scale of 1 to 5, with 5 being the highest amount of pain you have ever had."; "How is your energy level?"; "Are you socially withdrawn?"; "Have you been feeling anxious lately?"; etc. Further examples of potential questions are available, for example, in U.S. Pat. App. Pub. No. 2004/0138924, which is incorporated herein by reference.

If a subject engages the kiosk or other remote facility (e.g., by pushing a "START" button) but fails to answer at least one HQ, then one or more remote sensors may assist in determining if the subject is fully conscious, or able to proceed with the process. For example, a camera may determine if the subject is in pain, appears to be having a seizure or stroke, appears to be intoxicated, or is not fully conscious. At least a portion of the image is compared to various parameters and databases for signs of trauma, evaluation of appearance (skin, hair, nails, etc.), movement and cognition. At least a portion of the image is optionally compared with medical history by way of facial recognition.

In an embodiment, the kiosk transmits a notification relating to the request or voucher set forth by the subject. For example, a red light/green light or audio notice may provide notice that the voucher is not valid, not functioning properly. In another example, the notice provides verification that the voucher is valid and is functioning properly and the request for the medical product or service is being processed.

In an embodiment, the subject utilizes a "smart" dispenser for his/her individual use, which is able to electronically communicate with the kiosk or other remote facility. For example, the "smart" dispenser is able to wirelessly (e.g., via Bluetooth, flash drive, etc.) upload and/or download information to the kiosk. In another example, the "smart" dispenser is able to communicate (e.g., electronically, by audiovisual mode, or other mode) with the kiosk for obtaining or requesting a medical product or service.

As shown in FIG. 1, the system 100 includes at least one input/output device 117 either secured to a wall or movable (such as on a table or counter), optionally including a head sensor 118, and each can include data input such as for example one or more of keyboard input, mouse trackball or touchpad input, speech input, or audio/video input. In an embodiment, the input/output device includes a printer, fax, or scanner (120 indicates a printer/fax/scanner combination). In an embodiment, output includes a printed voucher for the subject to receive a requested product or service. As indicated, one or more sensors 102, 118, are located in proximity to or in directly contact with the subject 104. The optional location indicator 119 (shown as an armband) for determination by the kiosk or kiosk network of the subject's location and optionally allows for notification to the subject if the subject is instructed to exit the kiosk and seek medical attention elsewhere, or obtain the requested medical product or service at another location. In an embodiment, the optional location indicator can map where the subject is located and where the subject should travel to obtain the requested medical service or product.

As indicated, in an embodiment, the input/output device (including a keyboard, audio/video, or other device) includes a receiver 106 (optionally wireless, shown on camera), transceiver 108 (optionally wireless), transmitter 110 (optionally wireless), includes audio/video capabilities (e.g., camera 114), includes a power source 115, and memory 116. In an embodiment, the input/output device 117 is operably coupled to a computer device 112.

In an embodiment, a code acceptor 160 is included in the system 100. For example, the code acceptor 160 can include a voucher scanner, a fingerprint swiper, an iris scanner, a driver's license scanner, a bar code scanner, a QR scanner, keyboard, or other code acceptor.

In an embodiment, the system includes circuitry having one or more components operably coupled (e.g., communicatively, electromagnetically, magnetically, ultrasonically, optically, inductively, electrically, capacitively coupled, or the like) to each other. In an embodiment, circuitry includes one or more remotely located components. In an embodiment, remotely located components are operably coupled via wireless communication. In an embodiment, remotely located components are operably coupled via one or more receivers 106, transceivers 108, or transmitters 110, or the like.

In an embodiment, circuitry includes, among other things, one or more computing devices such as a processor (e.g., a microprocessor), a central processing unit (CPU), a digital signal processor (DSP), an application-specific integrated circuit (ASIC), a field programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In an embodiment, circuitry includes one or more memory devices 116 that, for example, store instructions or data. For example in an embodiment, the automated data collection system 100 includes one or more memory devices 116 that store information related to one or more characteristics of the subject that has been assessed, electronic health records, self-reported symptoms, insurance, or other health-related information. Non-limiting examples of one or more memory devices 116 include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like, persistent memory or the like, Erasable Programmable Read-Only Memory (EPROM), flash memory, or the like. The one or more memory devices 116 can be coupled to, for example, one or more computing devices 112 by one or more instructions, data, or power buses.

In an embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operably coupled to at least one computing device to control (electrical, electromechanical, software-implemented, firmware-implemented, or other control, or combinations thereof) at least one parameter associated with, for example, the health information related to the subject's health condition.

In an embodiment, the system is configured to operate in an application service provider format. In an embodiment, the system is configured to be implemented using open source tools. For example, in an embodiment, the system includes using one or more of Java, Java server pages (JSP), Java database connectivity (JDBC), structured query language (SQL), extensible markup language (XML), user interface language (XUL) and/or scalable vector graphics (SVG) technologies.

In an embodiment, image-based applications such as viewers and/or toolkits (e.g., Insight Segmentation and Registration Toolkit (ITK)), are incorporated for further intake of information. In an embodiment, CAD implementations or image segmentation may allow previous processing of images previously accepted on intake of information from the subject.

In an embodiment, circuitry includes a computer-readable media drive or memory slot that is configured to accept non-transitory signal-bearing medium (e.g., computer-readable memory media, computer-readable recording media, or the like). In an embodiment, a program for causing a system to execute any of the disclosed methods can be stored on, for example, a computer-readable recording medium (CRMM), a non-transitory signal-bearing medium, or the like. Non-limiting examples of signal-bearing media include a recordable type medium such as magnetic tape, floppy disk, a hard disk drive, Compact Disc (CD), a Digital Video Disk (DVD), Blu-Ray Disc, digital tape, computer memory, or the like, as well as transmission type medium such as a digital and/or analog communication medium (e.g., fiber optic cable, waveguide, wired communications link, wireless communication link (e.g., receiver 106, transceiver 108, or transmitter 110, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, cloud, or the like.

In an embodiment, the ADC system 100 includes circuitry having one or more modules optionally operable for communication with one or more input/output components that are configured to relay user output/input. In an embodiment, a module includes one or more instances of electrical, electromechanical, software-implemented, firmware-implemented, or other control devices. Such devices include one or more instances of memory, computing devices, antennas, power or other supplies, logic modules or other signaling modules, gauges or other such active or passive detection components, piezoelectric transducers, shape memory elements, micro-electro-mechanical systems (MEMS) elements, or other actuators.

In an embodiment, the computing device further includes audio/visual input/output connected to the system and configured to interact with the subject. In an embodiment, the system further includes a printing device connected to the computing device. In an embodiment, the system includes an input/output device including a graphical interface (e.g., display, touch screen, etc.).

In an embodiment, the one or more sensors include, for example, one or more acoustic sensors, optical sensors, electromagnetic energy sensors, image sensors, photodiode arrays, charge-coupled devices (CCDs), complementary metal-oxide-semiconductor (CMOS) devices, transducers, optical recognition sensors, infrared sensors, radio frequency component sensors, thermo sensors, three-dimensional sensors (e.g. to assess the subject's facial expressions exhibiting pain or discomfort, flushing or redness, or a subject's gait or other movements, etc.).

In an embodiment, one or more components of the system (e.g., chair impregnated with sensors for assessing one or more characteristics of the subject) operate in a networked environment using logic connections to one or more remote computing devices (e.g., a common network node, a network computer, a network node, a peer device, a personal computer, a router, a server, a tablet PC, a tablet, etc.) and typically includes many or all of the elements described above. In an embodiment, the logic connections include connections to a local area network (LAN), wide area network (WAN), and/or other networks. In an embodiment, the logic connections include connections to one or more enterprise-wide computer networks, intranets, and the internet. In an embodiment, the system 100, the one or more components of the system, or the like operate in a cloud computing environment including one or more cloud computing systems (e.g., private cloud computing systems, public cloud computing systems, hybrid cloud computing systems, or the like).

In an embodiment, the subject 104 includes a fetus. In an embodiment, the subject includes a human being. In an embodiment, the human being includes a fetus. In an embodiment, the subject includes a living organism that is distinguished from plants by independent movement and responsive sense organs.

In an embodiment the one or more sensors 102 may sense heartbeat intervals and ECG readings remotely by measuring small electrical potentials using a high input impedance electrometer. An example of such a sensor device is described in U.S. Patent Application Pub. No. 2006/0058694, supra; WO 2003/048789, supra; Harland, Meas. Sci. Technol., supra; Prance, 2007 Journal of Physics: Conference Series, supra, each of which is incorporated herein by reference. Such sensor devices are expected to provide noninvasive and remote monitoring. In an embodiment, the one or more sensors 102 may be worn by the subject in or on clothing or jewelry, such as in wrist bands, and may be in non-conductive contact with the body. For example, as described by U.S. Patent Application Pub. No. 2006/0058694, supra; WO 2003/048789, supra; C. J. Harland et al., 14 Meas. Sci. Technol. 923-928 (2003), each of which is incorporated herein by reference. In an embodiment, the one or more sensors 102 may be included in or associated with a piece of furniture, such as a chair or desk, or electronics such as a personal computer, or with some other remote item within, e.g., within approximately one meter from the subject. In an embodiment, the one or more sensors 102 are able to measure electric potentials may be embedded in objects, such as a bed or chair, in direct but non-conductive contact with the subject. For example, as described by U.S. Pat. No. 7,245,956, supra, each of which is incorporated herein by reference. In an embodiment, the one or more sensors 102 may sense heartbeat intervals and electrocardiographic information by examining physiologic activity of the subject or its organs and may be operable to sense a characteristic of the subject 104 in response to an electromagnetic signal sent at or illuminating the subject and reflected from the subject. In an embodiment, the illuminating may include exposing, subjecting, or directing energy at the subject. Systems using illuminating or reflected electromagnetic signals, including radiofrequency (RF) or microwave signals, are described in U.S. Pat. No. 7,272,431; U.S. Patent Application Pub. No. 2004/0123667; or U.S. Patent Application Pub. No. 2008/0045832; each of which is incorporated herein by reference. In an embodiment, one or more sensors 102, which may be or include a sensor array, may be deployed, for example, throughout a room, perhaps as part of a smart room network, so as to monitor the subject at rest or in motion.

In an embodiment, information gathered by the one or more sensors 102 may be communicated to a computer. In an embodiment, information may be communicated to a computer of the system electronically. In an embodiment, information may be communicated to a computer of the system wirelessly, for example using radio waves or ultrasound waves, or Bluetooth™ technology. In an embodiment, a computer, may be used to process the information. The computer may be part of a network.

As illustrated in FIG. 1, in one embodiment a system 100 for delivering medical products or services includes one or more sensors 102 configured to assess a subject 104. As shown, the subject 104, can be assessed by various modes, including but not limited to, input/output device (e.g., user interface) 117, sensor (e.g., breathalyzer, thermal scan, respiration sensor, pupillometry, retinal scan, etc.) 118, audio/visual device 114 (e.g., camera), optionally including one or more of a receiver 106, transceiver 108, transmitter 110, computer device 112, memory 116, or power source 115.

In an embodiment, the one or more sensors 102 includes a sensor array configured to sense a characteristic of the subject 102 without physically contacting the subject. For example, the sensor array may include at least two sensor heads. In an embodiment, the at least two sensor heads may include at least two sensor heads configured to sense the same characteristic of the subject. In an embodiment, the at least two sensor heads may include sensor heads configured to sense different characteristics of the subject. For example, one sensor head may be configured to sense temperature, another sensor head configured to sense heart rate, and a further sensor head configured to sense blood pressure. In an embodiment, the sensor includes a sensor responsive, without physically contacting the subject, to an impedance, capacitance, permittivity, reflectivity, absorption, or electrical activity of the subject. For example, a sensor including a capacitive proximity sensor element configured to sense a characteristic of a subject without physically contacting the subject is described in U.S. Patent Application Pub. No. 2008/0246495, incorporated herein by reference. For example, in an embodiment, a reflection or reflectivity characteristic may include an acoustic, light, or radio wave reflectivity. In an embodiment, the sensor includes a sensor responsive to the characteristic of a subject without physically contacting the subject. In an embodiment, the sensor includes a sensor configured to sense a characteristic of a subject, for example, at least one anatomical or physiological characteristic. The characteristics measured include steady state characteristics (e.g., height, weight, etc.), and variable characteristics (e.g., heart rate, blood oxygen level, etc.).

In an embodiment, the one or more sensors 102 includes a sensor configured to sense an Evaluated Criteria of the subject 104 without physically contacting the subject. For example, the sensor may be configured for an association with a chair, a pillow, or a gurney. In an embodiment of this sensor, the sensor may include a sensor configured for a physical association with an article of clothing or garment wearable by a subject and to sense a characteristic of the subject without physically contacting the subject. In an embodiment of this sensor, the sensor may include a sensor configured for a physical association with an object wearable by a subject and to sense a characteristic of the subject without physically contacting the subject. For example, the sensor may be configured for a physical association with eye glasses or jewelry. For example, a sensor configured for a physical association with an object wearable by a subject is described by U.S. Patent Application Pub. No. 2006/

0058694, Electrodynamic sensors and applications thereof, to T. Clark et al.; WO 2003/048789, Electrodynamic sensors and applications thereof, by T. D. Clark et al.; or C. J. Harland et al., *High resolution ambulatory electrocardiographic monitoring using wrist-mounted electric potential sensors,* 14 Meas. Sci. Technol. 923-928 (2003), each of which is incorporated herein by reference.

In an embodiment, the one or more sensors 102 include a sensor device configured to sense an Evaluated Criteria of the subject 104 without physically touching the subject. In an embodiment, the sensor device includes a sensor device configured to sense an Evaluated Criteria of a subject without a resistive contact with the subject. In an embodiment, the sensor device includes a sensor device configured to sense an Evaluated Criteria of a subject without an electrically conductive contact with the subject. In an embodiment, the sensor device includes a sensor device configured to sense an Evaluated Criteria of a subject across a non-electrically conductive gap with the subject.

In an embodiment, the sensor device includes an electrodynamic sensor device configured to sense an electrical activity of the heart of a subject without physically contacting the subject. For example, the electrodynamic sensor may be configured to sense a heart rate, electrical activity of the heart, such as electrocardiography (ECG), or conductivity. An example of a high input impedance electrodynamic sensor device configured to sense an electrical activity of a heart of a subject without physically contacting the subject is described in U.S. Patent Application Pub. No. 2006/0058694; WO 2003/048789, supra; Electrodynamic sensors and applications thereof, to T. Clark et al. In an embodiment, the sensor device includes an adaptive electric potential sensor device configured to sense a characteristic of a subject without physically contacting the subject. An example of an adaptive electric potential sensor device configured to sense a characteristic of a subject without physically contacting the subject is described in R. L. Prance et al., *Adaptive Electric Potential Sensors for smart signal acquisition and processing,* 76 Journal of Physics: Conference Series, 012025 (2007). In an embodiment, the sensor device includes an electric potential probe sensor device configured to sense a characteristic of a subject without physically contacting the subject. An example of an electric potential probe sensor device configured to sense a body electrical activity or signals, such as for example arterial pulse or other body electrodynamics, of a subject without physically contacting the subject is described in C. J. Harland et al., 13 *Meas. Sci. Tech.* 163-169 (2002).

In an embodiment, the one or more sensors 102 include a sensor configured to sense at least one of an electrical, acoustic, thermal, radiative, absorption, reflection, gaseous emission, or transmissibility Evaluated Criteria of the subject. In an embodiment, a thermal Evaluated Criteria may include an infrared measured thermal characteristic. In an embodiment, a thermal Evaluated Criteria may include microwave length (3-30 cm) electromagnetic radiation naturally emitted by the subject. For example, a sensor configured to sense a thermal Evaluated Criteria of the subject includes a microwave radiometer operable to measure natural electromagnetic radiation from the subject's internal tissue in the microwave range. In an embodiment, the microwave radiometer may be combined with an infrared sensor as described in R. Avagyan et al., *New diagnostic methods in acupuncture,* ICMART '99 International Medical Acupuncture Symposium 7, Riga, (May 21-23, 1999), each of which is incorporated herein by reference. See also, Pub. No. WO 2006/091123 (PCT/RU2006/000072), each of which is incorporated herein by reference. For example, a transmissibility characteristic may include a light or radio wave transmissibility characteristic of the subject that is utilized as an Evaluated Criteria. For example, in an embodiment, a radiative characteristic may include gammas or other types of radiation emitted by the body of the subject him/herself, for example potassium 40. An embodiment of a gamma-ray sensor device configured to sense a characteristic of a subject without physically contacting the subject is expected to be provided by the Radtell™ passive gamma-ray sensor by Oak Ridge National Laboratory of Oak Ridge, Tenn.

In an embodiment, a sensor 102 is operably coupled to one or more sensor control units 134. In an embodiment, the one or more sensor control units 134 serve to regulate the activity of the one or more sensors 102. For example, in an embodiment, one or more sensor control units 134 regulate one or more times when the one or more sensors 102 detect one or more signals from the subject that are related to one or more Evaluated Criteria of the subject. In an embodiment, the one or more sensor control units 134 regulate one or more time periods when one or more sensors 102 detect one or more signals from the subject that are related to one or more Evaluated Criteria of the subject.

In an embodiment, a sensor 102 is configured to wirelessly communicate sensed electrical signals originating from a subject. In an embodiment, a sensor 102 is electrically or optically coupled to the control circuitry to communicate the one or more signals thereto. In an embodiment, a sensor 102 includes one or more sensor housings 144. In an embodiment, one or more sensor housings 144 are operably coupled with the one or more sensors 102.

In an embodiment, numerous types of sensors 102 can be operably coupled to the computing device 112. Examples of such sensors 102 include, but are not limited to, electrodes, surface plasmon resonance detectors, microelectromechanical systems detectors, microcantilever detectors, nitric oxide detectors, osmotic detectors, relativity-based detectors, chemical detectors, pressure detectors, electrochemical detectors, piezoelectric detectors, pH detectors, hydrogel detectors, enzymatic detectors, ball integrated circuit detectors, affinity viscosimetric detectors, blood pressure detectors; metal detectors, glucose detectors, and the like (e.g., U.S. Pat. Nos. 7,162,289; 6,280,604; 5,603,820; 5,582,170; 6,287,452; 7,291,503; 6,764,446; 7,168,294; 6,823,717; 7,205,701; 6,268,161; 4,703,756; 6,965,791; 6,546,268; 6,210,326; 6,514,689; 6,234,973; 6,442,413; Tu et al., Electroanalysis, 11:70-74 (1999), each of which is incorporated herein by reference). In an embodiment, one or more detectors 136 are configured to detect one or more of pH, chemicals, or nerve signals from the subject.

In an embodiment, one or more sensor housings 144 include circuitry that is operably coupled to one or more sensors 102. In an embodiment, one or more sensor housings 144 include circuitry that is configured to facilitate elimination of one or more sacrificial layers. In an embodiment, one or more sensor housings 144 include circuitry that is configured to be operably coupled to one or more sensor control units 134. In an embodiment, one or more sensor housings 144 include circuitry that is configured to be operably coupled to one or more sensor power sources 115. In an embodiment, one or more sensor housings 144 include circuitry that is configured to be operably coupled to one or more sensor receivers 106. In an embodiment, one or more sensor housings 144 include circuitry that is configured to be operably coupled to one or more sensor transmitters 110.

In an embodiment, a sensor 102 includes one or more sensor power sources 115 (including but not limited to batteries). In an embodiment, a sensor 102 is operably coupled to one or more sensor batteries 115. In an embodiment, a sensor battery 115 includes a thin-film fuel cell such as a solid oxide type (SOFC), a solid polymer type (SPFC), a proton exchange membrane type (PEMFC), and/or substantially any combination thereof. Methods to fabricate such thin-film fuel cells are known and have been described (e.g., U.S. Pat. No. 7,189,471, incorporated herein by reference). In an embodiment, one or more sensor batteries 115 include one or more storage films that are configured for energy storage and energy conversion. Methods to fabricate such storage films are known and have been described (e.g., U.S. Pat. No. 7,238,628, incorporated herein by reference). In an embodiment, a sensor battery 115 is a biobased battery (e.g., U.S. Pat. No. 6,994,934, incorporated herein by reference). In an embodiment, one or more sensor batteries 115 are thin-film batteries. Methods to fabricate thin-film batteries, including thin film microbatteries, are known and have been described (e.g., U.S. Pat. Nos. 5,338,625, 7,194, 801; 7,144,655; 6,818,356, incorporated herein by reference). In an embodiment, one or more sensor electromagnetic receivers (not shown) are used to electromagnetically couple power to energize one or more sensors 102 from an external power source 115. Methods to construct electromagnetic receivers have been described (e.g., U.S. Pat. No. 5,571,152), incorporated herein by reference. In an embodiment, the receiver and/or transmitter are not part of the sensor.

In an embodiment, the system 100 includes one or more sensor transmitters 110. Numerous types of transmitters 110 can be used in association with system 100. Examples of such transmitters 110 include, but are not limited to, transmitters that transmit one or more acoustic signals, optical signals, radio signals, wireless signals, hardwired signals, infrared signals, ultrasonic signals, and the like (e.g., U.S. Pat. Nos. RE39,785; 7,260,768; 7,260,764; 7,260,402; 7,257,327; 7,215,887; 7,218,900), each of which is incorporated herein by reference. In an embodiment, one or more sensor transmitters 110 may transmit one or more signals that are encrypted. Numerous types of transmitters are known and have been described (e.g., U.S. Patent Nos. and Published U.S. Patent Applications: U.S. Pat. Nos. 7,236, 595; 7,260,155; 7,227,956; US2006/0280307), incorporated herein by reference.

In an embodiment, the system 100 includes one or more sensor receivers 106. Numerous types of sensor receivers 106 may be used in association with system 100. Examples of such sensor receivers 106 include, but are not limited to, receivers that receive one or more acoustic signals, optical signals, radio signals, wireless signals, hardwired signals, infrared signals, ultrasonic signals, and the like. Such receivers 106 are known and have been described (e.g., U.S. Pat. Nos. RE39,785; 7,218,900; 7,254,160; 7,245,894; 7,206, 605), incorporated herein by reference.

In an embodiment, the system 100 includes a locked drop box 136 that is optionally electronically connected to the computing device 112. In an embodiment, one or more compartments 145 hold various medical products or services that may be sought by a subject 104. In an embodiment, the system 100 includes a dispensing box 142 optionally where the medical product or service is dispensed. In an embodiment, the product or service is retrieved directly from the compartment 145 where it is located. In an embodiment, the compartment 145 is configured with at least one means for alerting the subject 104 that the medical product or service is located in that compartment 145 and is ready to be retrieved (e.g., by opening the compartment door). In an embodiment, the means for alerting the subject includes at least one audio, visual, or tactile alert such as, for example, a light, beeping, buzzing, vibration, or other similar alert. In an embodiment, the system 100 further includes a printer/ scanner/fax 120. In an embodiment, the system 100 includes a currency exchanger or acceptor 140. In an embodiment, a privacy curtain/door 150 allows for privacy while the subject 104 uses the system 100. In an embodiment, a pillbox device 155 is configured to be engaged with the computing device 112, by a port for example, by way of a wired connection, flash drive (USB), Microdrive, or wireless connection. In an embodiment, the pillbox includes at least one compartment (e.g. closable compartment) operably coupled with circuitry configured for sending a signal when the compartment is engaged (e.g., opened, drug dispensed into the compartment, etc.).

Various statistical programs or computer algorithms for simulating systems may be implemented with various embodiments described herein. For example, ANOVA, Monte Carlo, etc., and other programs may be implemented.

In an embodiment, a signal can be an external signal 188. Examples of such signals include, but are not limited to, analog signals, digital signals, acoustic signals, optical signals, radio signals, wireless signals, hardwired signals, infrared signals, ultrasonic signals, and the like. In an embodiment, one or more signals may not be encrypted. In an embodiment, one or more signals may be encrypted. In an embodiment, one or more signals may be sent through use of a secure mode of transmission. In an embodiment, one or more signals may be coded for receipt by a specific subject. In an embodiment, such code may include anonymous code that is specific for a subject. Accordingly, information included within one or more signals may be protected against being accessed by others who are not the intended recipient.

As shown in FIG. 1, in an embodiment describing methods, systems, and computer program products described herein, one or more subjects engage with the kiosk for redemption of a voucher or request of one or more medical products or services.

In an embodiment, at least one dataset described herein includes a dynamic data structure. In an embodiment, at least one dataset described herein includes a static data structure. In an embodiment, a subject is assessed based on queries of the Evaluated Criteria that form a data structure and that may be utilized to determine an overall Health Status Indicator value. In an embodiment, the query includes at least one of a question of the subject, observed or sensed Criteria, or input based on the subject's health history or health records. In an embodiment, the query includes a survey from an input/output device, for example. In an embodiment, the survey can be in any language, or in pictorial or other form. In an embodiment, the survey includes skip logic, or conditional branching, that allows for the survey to be customized for the subject based on the subject's previous responses. For example, if a subject's first query includes asking whether the subject is male or female, and the subject answers "female," then the survey skip logic rules could be such that it forces the subject to skip questions related to exclusively male symptoms or conditions.

In an embodiment, a particular Evaluated Criteria value is coupled to the Health Status Indicator value more tightly than another particular Evaluated Criteria value. For example, a heavier weight might be given to tightly coupled Evaluated Criteria to corresponding Health Status Indicator values (e.g., heart rate, respiration, etc.). In an embodiment, one or more Evaluated Criteria values are weighted heavier, thus generating a higher value when included in the subject's response, and tipping the analysis toward granting the request by the subject, if an evaluation is needed for the request. For example, a heavier weight can be given to a characteristic that is sensed or present in the subject's health records, and a lesser weight to a self-reported characteristic, particularly when the data collected appears to be contradictory or inconsistent.

In an embodiment, no or minimal evaluation of the subject is required in order to grant the request of the medical product or service (e.g., band-aid request, 2 pills of ibuprofen request, etc.), while moderate or high evaluation of the subject is required in order to grant other requests (e.g., pregnancy test request, statin request, etc.), and certain requests will require that the subject seek additional medical treatment and will not be granted under any circumstances or will only be granted by way of a subject previously obtaining a voucher from a healthcare provider (e.g., narcotics request, etc.).

As shown in FIG. 1, the system 102 includes a computing device 112 with optionally one or more of a receiver 106, transceiver 108, transmitter 110, memory 116, or power source 115. In an embodiment, as described, the dynamic dataset includes a compilation of data from each assessed subject in the queue. For example, Subject is assessed, generating ABC data (one or more Evaluated Criteria values based on one or more assessed characteristics of the subject), which provide the basis for generation of a Health Status Indicator value for Subject based on the Evaluated Criteria value dataset, the ABC data enters the Evaluated Criteria dataset for that subject. In an embodiment, this information is immediately uploaded so that any kiosk or remote access delivery station in the network is updated and the subject is disallowed from engaging a second kiosk for the same request that was just fulfilled or rejected.

Figure 2:
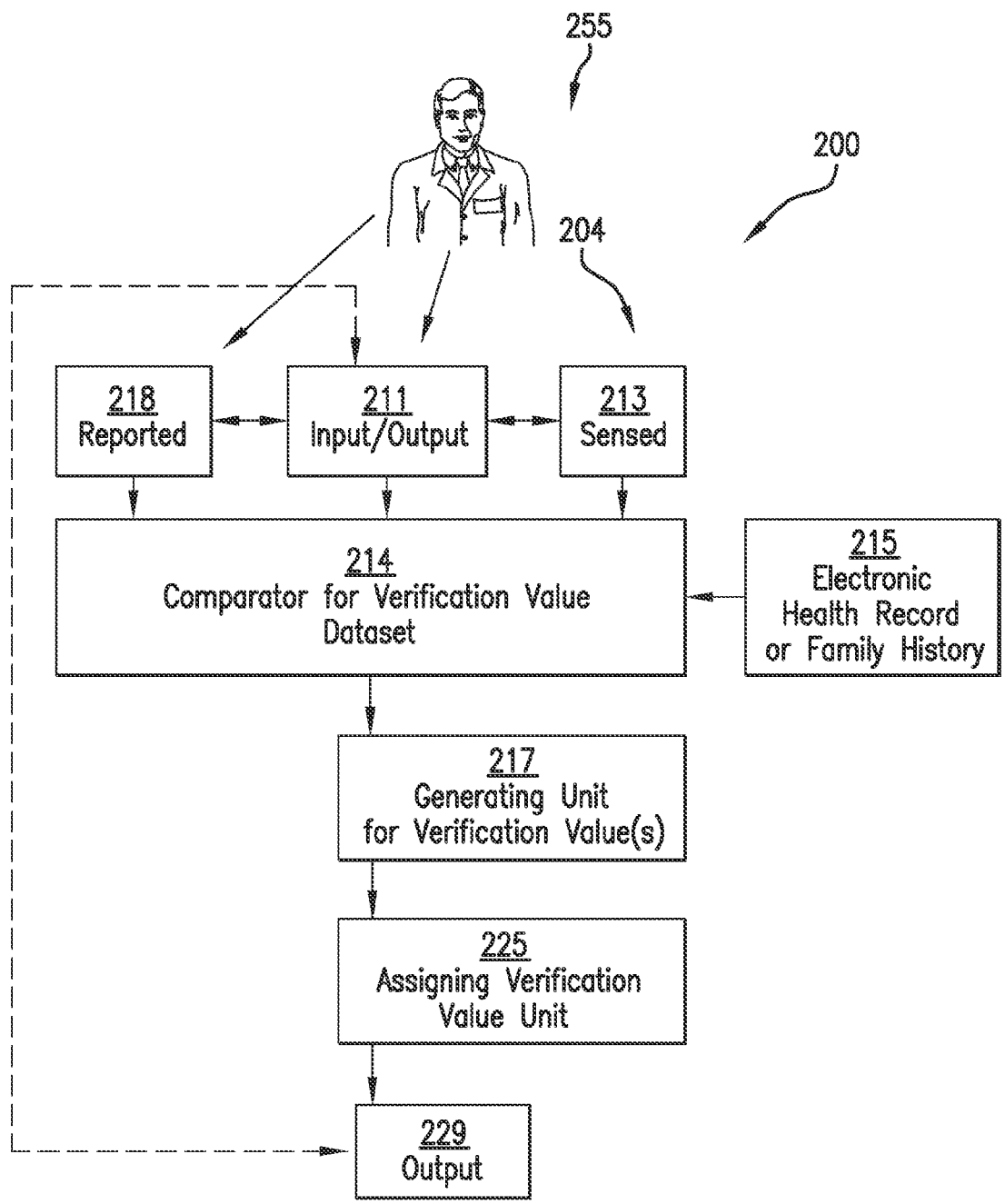
FIG. 2 illustrates a partial view of an embodiment disclosed herein.

FIG. 2 illustrates one embodiment that includes a system 255 including at least one computing device 200. The computing device can take various forms or be part of an object, such as a limited resource computing device, a wireless communication device, a mobile wireless communication device, an electronic pen, a handheld electronic writing device, a digital camera, a scanner, an ultrasound device, an x-ray machine, a noninvasive imaging device, a cell phone, a PDA, an electronic tablet device, a medical apparatus (implantable or otherwise), a printer, a car, and an airplane.

The computing device 200 is operably connected to at least one input/output device (see other Figures) for which the subject 204 can interact. For example, in an embodiment, the system 255 includes and input/output device 211, which includes a non-transitory signal bearing medium operable to interact with a user 218 (can be self-reported information, sensed information, or information obtained from health history records or family members, etc. given to a health care worker, a subject may self-report or an assistant may report on behalf of the subject) and receive input relating to the subject's seeking a medical product or service. In an embodiment, the input/output device 211 includes a non-transitory signal bearing medium operable to compare the at least one input from the subject relating to the subject's attempt to attain a medical product or service with one or more verification datasets, as described herein, and generate a verification value based on the comparison, and optionally reinitiate receiving at least one additional input from the subject, and optionally repeating the comparing step and generating a verification value. In an embodiment, the non-transitory signal bearing medium is operable to reinitiate receiving at least one additional input from the subject until a verification threshold is satisfied or denied and communicate the output indicative of the verification value. In an embodiment, the output includes at least one of a visual cue, audio cue, or tactile cue. In an embodiment, the input/output device is operable to convert input into electronic signals that include digitized or weighted protocols.

In an embodiment, the verification datasets include one or more of an inventory dataset, an electronic medical record for the subject dataset, a verification code dataset, or health status indicator dataset. In an embodiment, the input includes at least one input in response to one or more queries. In an embodiment, the input includes at least one detected physiological parameter or characteristic, such as an electrical measurement, biochemical measurement, or thermal measurement, by way of one or more sensors.

In an embodiment, the input includes input from a data storage device, such as a USB, CD, DVD, or similar storage device. Likewise, input may be provided related to the subject's seeking a medical product or service by way of a mobile phone, computer tablet, computer laptop, or other computing device.

In addition, if one or more sensors are employed, information is sensed 213. The system 255 further includes a comparator for the Verification value dataset 214, which is operably coupled to electronic health records or family health history 215. In an embodiment, the system 255 further includes at least one Generating Unit 217 for one or more Verification value(s) for the subject. In an embodiment, the system 255 includes an assigning Verification Value unit 225, and generates output 229 which may include the dispensing of the medical product or service being sought by the subject 204. In an embodiment, a signal can alert when the subject's verification value satisfies the verification threshold.

In an embodiment, the subject is further assessed for at least one symptom (either by way of being sensed by a sensor, self-reported, reported on behalf of the subject, retrieved from electronic health records, etc.) and comparing the evaluated symptom criteria with a health status dataset. This is particularly useful in cases when the subject does not have a pre-approved prescription. In an embodiment, the subject is assigned a health status indicator valued based on the comparison, and the system can signal an alert when the subject's health status indicator value satisfies a health status threshold.

In an embodiment, generating a verification value includes coordinating a medical symptom code or value as a function of satisfying the threshold condition. As described herein elsewhere, a characteristic or symptom of a subject may be coded thereby generating a medical symptom code.

In an embodiment, comparing the input includes coordinating at least one piece of identification information with an identification dataset as a function of the threshold condition. Identification information is described herein, and includes, for example, a fingerprint, driver's license, or other information specific to the identity of the subject seeking a medical product or service. In an embodiment, at least one input is stored.

In an embodiment, the system is further configured for transmitting one or more signals in response to communicating an output indicative of the verification value, which may include at least one of a tactile, audio, or visual representation. In an embodiment, the tactile representation includes at least one pattern of vibration (e.g., a pulse pattern or speed pattern). In an embodiment, the method and system further include recording and optionally storing the results of receiving at least one input from the subject and/or the verification value(s) of the subject. In an embodiment, the systems and methods described herein include recording a confirmation (e.g., audio, video, etc.) confirmation that the subject has taken or used the medical product or service. In an embodiment, the recording includes at least one of a time stamp, location stamp, subject name, medical product or service name or code, or drug dosage. In an embodiment, recording includes receiving an RFID signal associated with the medical product or service (e.g., the RFID signal indicates the package open or the drug swallowed).

As set forth in FIGS. 1-2, a subject makes a request that requires at least some evaluation, and provides at least one response (e.g., by query or sensor) that generates a verification value dataset (can be static or dynamic). From the verification dataset, the subject's verification value is determined, optionally including analysis of health history/records. As shown, if one or more of a subject's verification values exceeds a [predetermined] threshold, the subject's request is granted. As described herein, in an embodiment, the verification input includes subject's identification (driver's license, fingerprint, etc.). In an embodiment, the verification input includes identification as well as symptoms or health conditions (e.g., by way of evaluated criteria or sensed or reported symptoms or conditions). As described herein, in an embodiment, the subject presents a voucher for redemption, and no evaluation is needed.

In an embodiment, the subject requests a medical product or service, and one or more of a subject's Evaluated Criteria may or may not exceed a [predetermined] threshold, yet the subject's request requires further evaluation based on the criteria not exceeding the threshold, or indicating that further evaluation is required in order to grant the request.

Figure 3:
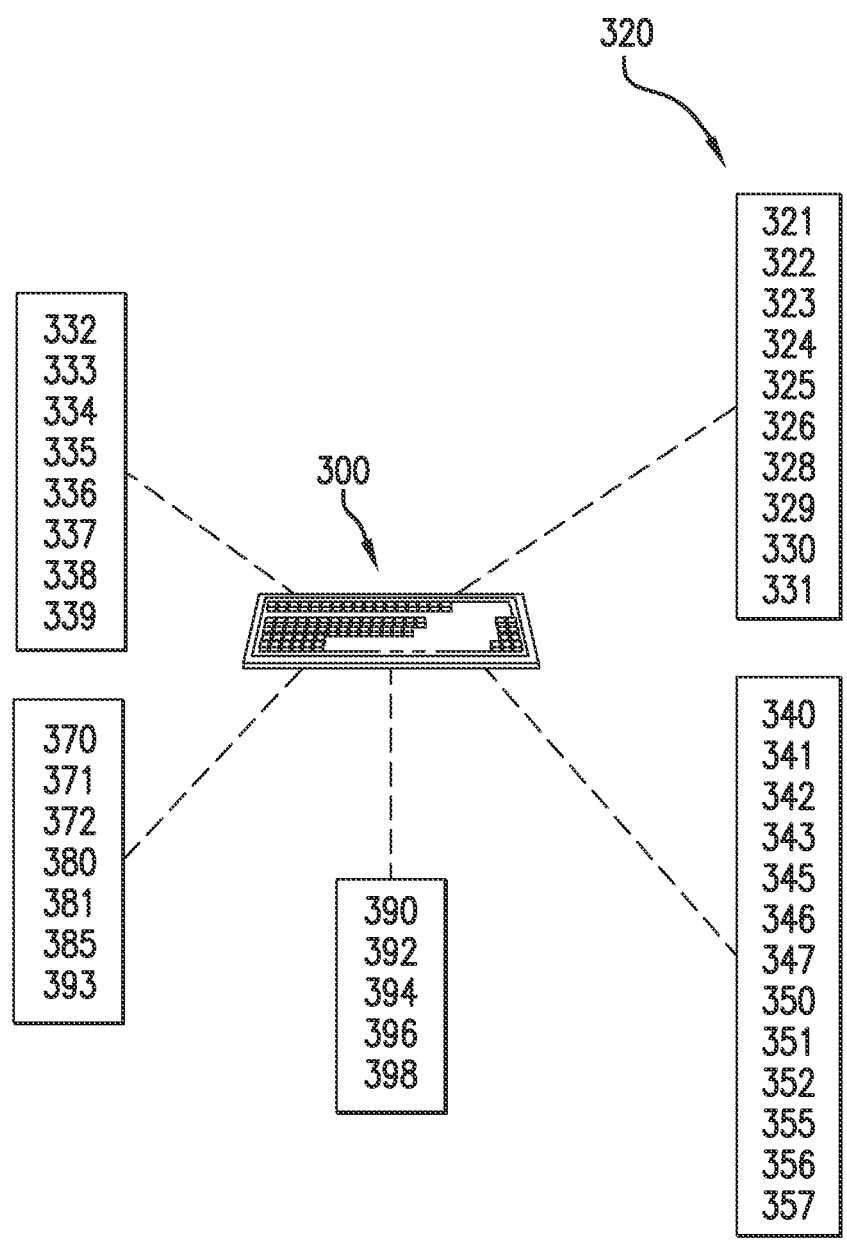
FIG. 3 illustrates a partial view of an embodiment disclosed herein.

FIG. 3 illustrates an input/output device 300 operably coupled with a computing device 320 that includes a processing unit 321, a system memory 322, and a system bus 323 that couples various system components including the system memory 322 to the processing unit 321. The system bus 323 may be any of several types of bus structures including a memory bus or memory controller, a peripheral bus, and a local bus using any of a variety of bus architectures. The system bus 323 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The system memory includes read-only memory (ROM) 324 and random access memory (RAM) 325. A basic input/output system (BIOS) 326, containing the basic routines that help to transfer information between sub-components within the thin computing device 320, such as during start-up, is stored in the ROM 324. A number of program modules may be stored in the ROM 324 or RAM 325, including an operating system 328, one or more application programs 329, other program modules 330 and program data 331.

A user may enter commands and information into the computing device 320 through input devices, such as a number of switches and buttons, illustrated as hardware buttons 344, connected to the system via a suitable interface 345. Input devices may further include a touch-sensitive display with suitable input detection circuitry, illustrated as a display 332 and screen input detector 333. The output circuitry of the touch-sensitive display 332 is connected to the system bus 323 via a video driver 337. Other input devices may include a microphone 334 connected through a suitable audio interface 335, and a physical hardware keyboard (not shown). Output devices may include at least one the display 332, or a projector display 336.

In addition to the display 332, the computing device 320 may include other peripheral output devices, such as at least one speaker 338. Other external input or output devices 339, such as a joystick, game pad, satellite dish, scanner or the like may be connected to the processing unit 321 through a USB port 340 and USB port interface 341, to the system bus 323. Alternatively, the other external input and output devices 339 may be connected by other interfaces, such as a parallel port, game port or other port. The computing device 320 may further include or be capable of connecting to a flash card memory (not shown) through an appropriate connection port (not shown). The computing device 320 may further include or be capable of connecting with a network through a network port 342 and network interface 343, and through wireless port 346 and corresponding wireless interface 347 may be provided to facilitate communication with other peripheral devices, including other computers, printers, and so on (not shown). It will be appreciated that the various components and connections shown are examples and other components and means of establishing communication links may be used.

The computing device 320 may be designed to include a user interface. The user interface may include a character, a key-based, or another user data input via the touch sensitive display 332. The user interface may include using a stylus (not shown). Moreover, the user interface is not limited to an actual touch-sensitive panel arranged for directly receiving input, but may alternatively or in addition respond to another input device such as the microphone 334. For example, spoken words may be received at the microphone 334 and recognized. Alternatively, the computing device 320 may be designed to include a user interface having a physical keyboard (not shown).

In certain instances, one or more components of the computing device 320 may be deemed not necessary and omitted. In other instances, one or more other components may be deemed necessary and added to the computing device.

In certain instances, the computing system typically includes a variety of computer-readable media products. Computer-readable media may include any media that can be accessed by the computing device 320 and include both volatile and nonvolatile media, removable and non-removable media. By way of example, and not of limitation, computer-readable media may include computer storage media. By way of further example, and not of limitation, computer-readable media may include a communication media.

Computer storage media includes volatile and nonvolatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 720. In a further embodiment, a computer storage media may include a group of computer storage media devices. In another embodiment, a computer storage media may include an information store. In another embodiment, an information store may include a quantum memory, a photonic quantum memory, or atomic quantum memory. Combinations of any of the above may also be included within the scope of computer-readable media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, RF, optical, and infrared media.

The computing device 320 may also include other removable/non-removable, volatile/nonvolatile computer storage media products. For example, such media includes a non-removable non-volatile memory interface (hard disk interface) 345 reads from and writes for example to non-removable, non-volatile magnetic media, or a removable non-volatile memory interface 350 that, for example, is coupled to a magnetic disk drive 351 that reads from and writes to a removable, non-volatile magnetic disk 352, or is coupled to an optical disk drive 355 that reads from and writes to a removable, non-volatile optical disk 356, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 357 is typically connected to the system bus 323 through a non-removable memory interface, such as the interface 345, and magnetic disk drive 351 and optical disk drive 355 are typically connected to the system bus 323 by a removable non-volatile memory interface, such as interface 350.

The drives and their associated computer storage media discussed above provide storage of computer-readable instructions, data structures, program modules, and other data for the computing device 320.

A user may enter commands and information into the computing device 320 through input devices such as a microphone, keyboard, or pointing device, commonly referred to as a mouse, trackball, or touch pad. Other input devices (not shown) may include at least one of a touch sensitive display, joystick, game pad, satellite dish, and scanner. These and other input devices are often connected to the processing unit through a user input interface that is coupled to the system bus, but may be connected by other interface and bus structures, such as a parallel port, game port, or a universal serial bus (USB).

The computing system may operate in a networked environment using logical connections to one or more remote computers, such as a remote computer 380. The remote computer 380 may be a personal computer, a server, a router, a network PC, a peer device, or other common network node, and typically includes many or all of the elements described above relative to the computing device 320, although only a memory storage device. The network logical connections include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing system is connected to the network 371 through a network interface, such as the network interface 370, the modem 372, or the wireless interface 393. The network may include a LAN network environment, or a WAN network environment, such as the Internet. In a networked environment, program modules depicted relative to the computing device 320, or portions thereof, may be stored in a remote memory storage device. By way of example, and not limitation, remote application programs 385 as residing on computer medium 381. It will be appreciated that the network connections shown are examples and other means of establishing communication link between the computers may be used.

In certain instances, one or more elements of the computing device 320 may be deemed not necessary and omitted. In other instances, one or more other components may be deemed necessary and added to the computing device 320.

The signal generator 390 includes a signal generator configured to generate a signal indicative of the sensed Evaluated Criteria of the subject. In an embodiment, the signal may include a raw data signal, i.e., a capacitance measurement, a change in position of skin over artery in the neck, an acoustic pressure, or a brain electrical activity of the subject. In an embodiment, the signal generator may include a processor circuit 392, a treatment regimen circuit 394, a treatment decision circuit 396, or a communications circuit 398. In an embodiment, the communications circuit may be operable to communicate using an electrical conductor or using a wireless transmission. In an embodiment, the signal generator may include an instance of the thin computing device 320 and the processor circuit may be the processing unit 321.

In an embodiment, the system actively monitors (e.g., detects, tracks, etc.) a subject located by using at least one of computerized axial tomography, fiber optic thermometry, infrared thermography, magnetic resonance imaging, magnetic resonance spectroscopy, microwave thermography, microwave dielectric spectroscopy, positron emission tomography, ultrasound reflectometry, spectroscopic imaging, visual imaging, infrared imaging, single photon emission computed tomography, or the like.

In an embodiment, the system includes a subject tracking system (not shown in figures). For example, in an embodiment, the system includes a subject tracking system for updating in real time a subject's virtual location in a virtual space corresponding to the physical location of the subject in a physical space, such as the doctor's office, airport, school, college campus, etc. In an embodiment, the subject's location relative to a locked dropbox or product/service dispensary port is tracked by the tracking system. In an embodiment, a map is provided to the subject to direct the subject to seek medical care elsewhere. In an embodiment, the subject tracking system includes an optical recognition distributed sensor network that generates Health Status Indicator value based in part on the continuous monitoring of the overall physical condition of the subject, including subject's movements, gait, etc., optionally as part of approval of the request or voucher redemption from the subject for the medical product or service.

Figure 4:
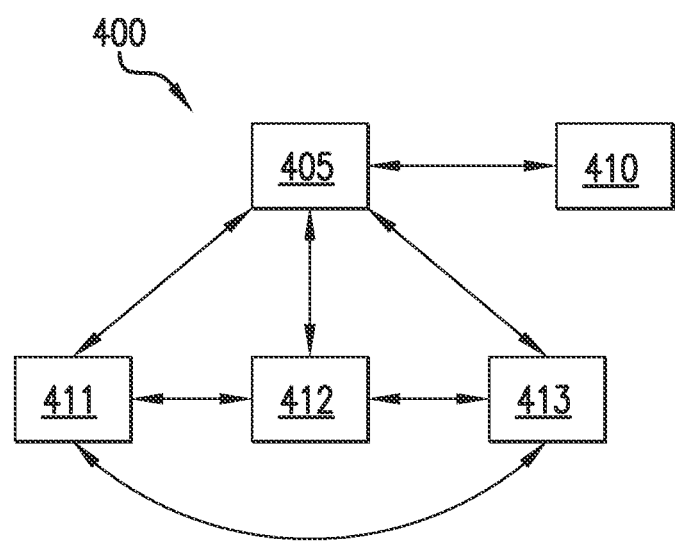
FIG. 4 illustrates a partial view of an embodiment disclosed herein.

As shown in FIG. 4, the system 400 includes one or more kiosks (each shown as 411, 412, and 413) that are operably linked to a central server 405 that is operably linked to hard drive storage 410. Each kiosk (411, 412, 413) includes, as described elsewhere herein, optional components that can further communicate with the central server 405, including but not limited to a printer/scanner/fax, currency acceptors, sensors for detecting particular characteristics of the subject, as well as an interactive menu for the subject to provide input related to the subject's seeking a medical product or service. In an embodiment, the central server 405 includes circuitry configured for setting up medical products or services that are equivalents to each other, should the subject request an equivalent. In an embodiment, the central server 405 includes circuitry configured for generating output information related to the subject's seeking a medical product or service. In an embodiment, the central server 405 includes circuitry configured for processing the approval, verifying the pre-approval, or assessing the subject by way of characteristic evaluation criteria. In an embodiment, the central server 405 includes circuitry configured for processing financial transactions, including accepting currency or credit card/debit card/online financial transactions for the medical product or service, or processing the insurance claim. In an embodiment, the central server 405 includes circuitry configured for determining inventory within each kiosk in the network, and for relaying information to a user or central re-stocking facility (not shown) in order to replenish inventory that is reaching pre-determined levels in any particular kiosk. In an embodiment, each kiosk signals the central server 405 when a particular medical product or service has reached a pre-determined level or after each dispensing of every medical product or service in real-time. In an embodiment, the central server 405 includes circuitry for monitoring security breaches at any of the kiosks in the network, and disables a kiosk that is suspected of being tampered with or whose security has been breached. In an embodiment, the central server 405 includes circuitry for communicating with each kiosk in determining the verification value of the subject and whether that value satisfies the verification threshold or not.

In an embodiment, each kiosk (411, 412, 413) includes circuitry for communicating with one or more sensors, one or more input/output devices, the central server, etc. and may include a user interface for interacting with a subject seeking a medical product or service. In an embodiment, a server interface (not shown) includes circuitry for transmitting or receiving data wirelessly between a kiosk and the central server.

Figure 5:
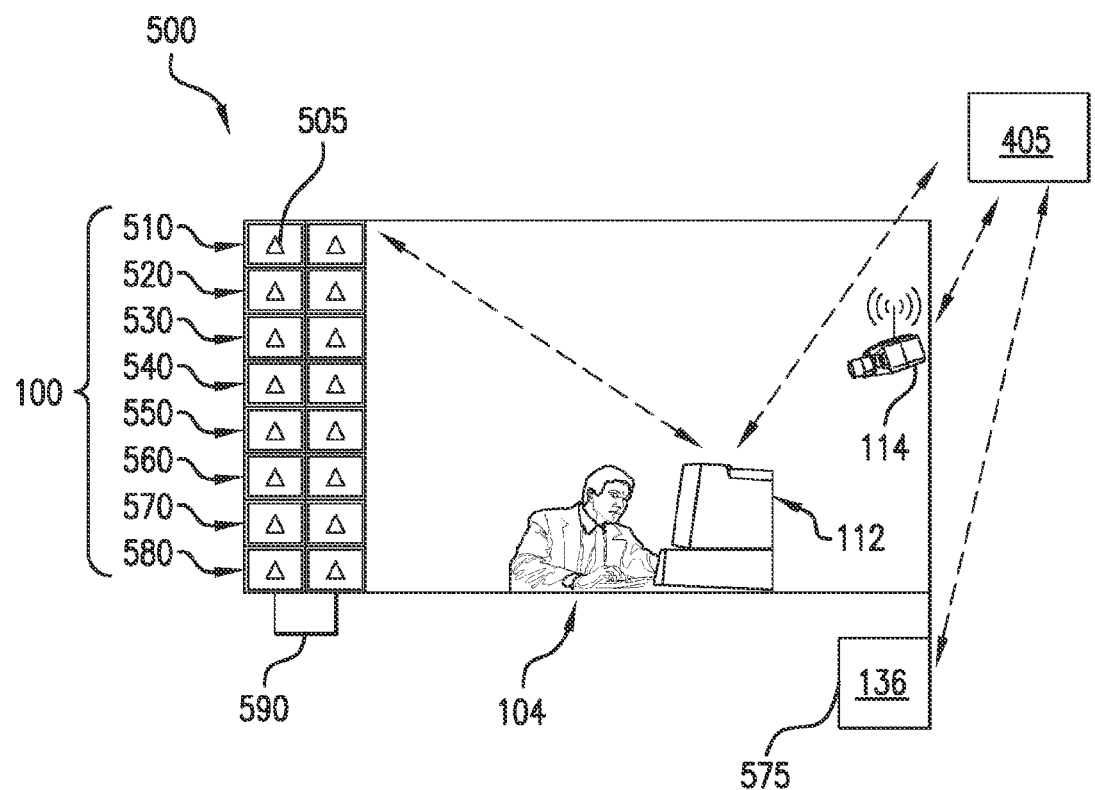
FIG. 5 illustrates a partial view of an embodiment disclosed herein.

As described in FIG. 5, in an embodiment, the system 500 includes a kiosk 100 with one or more compartments (510, 520, 530, 540, 550, 560, 570, and 580) optionally with each compartment holding a different medical product or service than any other compartment. In an embodiment, an opening or slot 505 is included with each compartment (510, 520, 530, 54, 550, 560, 570, 580) for dispensing of a medical product or service to a subject 104. In an embodiment, a central opening or slot 590 common to more than one compartment (510, 520, 530, 540, 550, 560, 570, 580) for dispensing of the medical product or service to the subject 104. In an embodiment, the common slot or opening 590 may be configured to dispense a medical product or service from a row, column, or other multiple compartments (510, 520, 530, 540, 550, 560, 570, 580). In an embodiment, the locked drop box 136 described previously also includes circuitry for transmitting or receiving data with the central server (dotted lines) and may include components such as security alarm sensors, camera 114, or electronic lock 575. In an embodiment, each kiosk 100, as described herein, includes multiple slots or openings (505, 590) where the medical product or service is dispensed upon satisfaction of the verification threshold. In an embodiment, the input/output device of the kiosk 100 is in electronic communication with one or more compartments (510, 520, 530, 540, 550, 560, 570, 580) and with the central server 405 (communication indicated by dotted lines). As indicated, the camera 114 and locked drop box 136 are also each in electronic communication (dotted lines) with the server 405.

Figure 6:
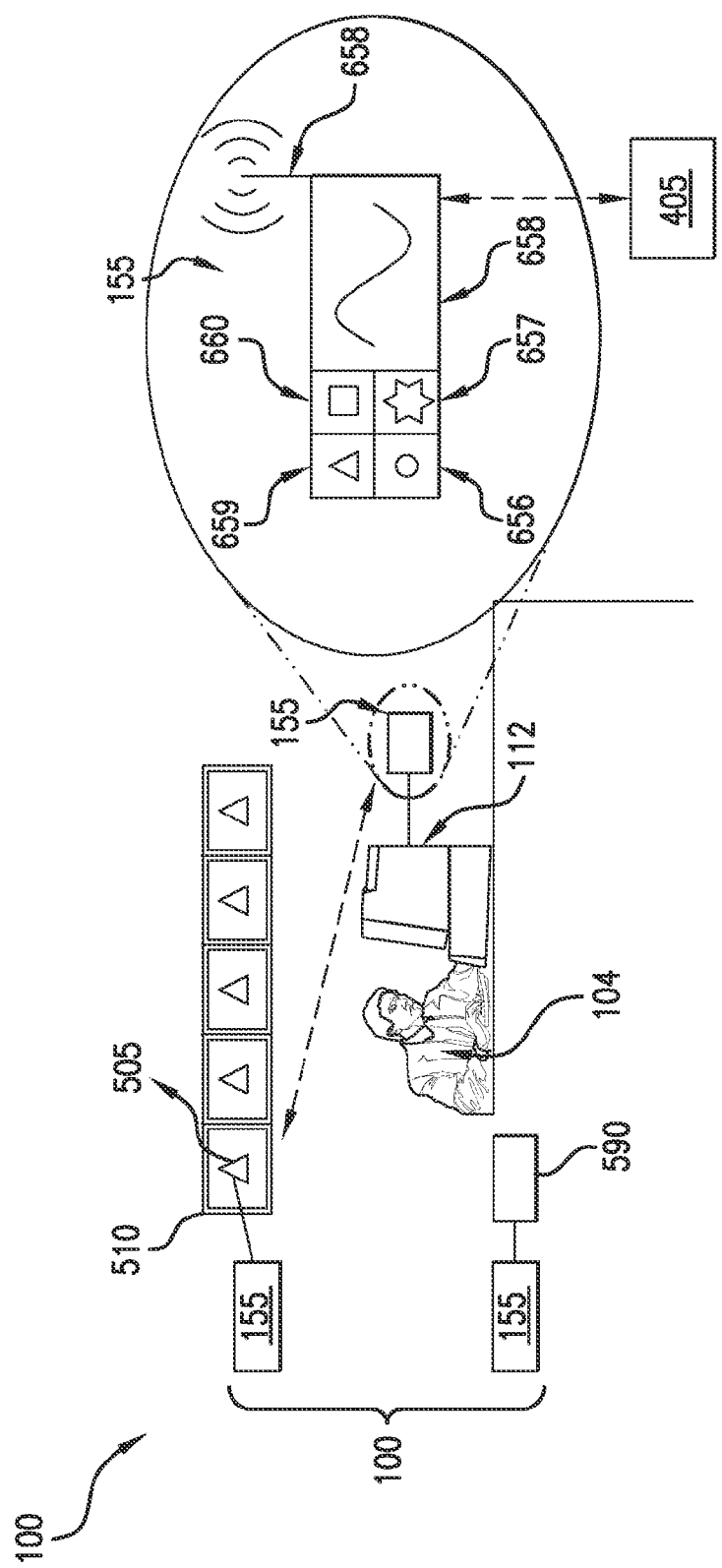
FIG. 6 illustrates a partial view of an embodiment disclosed herein.

As described in FIG. 6, the system 600 includes a kiosk 100 for which a subject 104 seeks a medical product or service by way of inserting a pillbox device 155 into the input/output device 112 of the kiosk 100. In an embodiment, the pillbox device 155 is configured to be inserted as a USB drive into the input/output device 112, and information is transferred between the pillbox device 155 and the server 405 (dotted lines) and optionally with one or more compartment 510 (dotted lines). In an embodiment, the pillbox device 155 can be inserted into the slot or opening 505 of a particular compartment 510. In an embodiment, the pillbox device 155 can be inserted into the common opening or slot 590 common to more than one compartment 510. As indicated, the pillbox device 155 includes one or more sectioned compartments (656, 657, 658, 659, 660) that can allow for dispensing of different pharmaceutical drugs (indicated by different symbols on each sectioned compartment). In an embodiment, the pillbox device includes a transmitter or receiver (indicated by the antenna 670) for communicating with one or more computing devices in the network such as at the kiosk 100 or with the server 405. In an embodiment, a GPS or other locator is included as part of the pillbox device.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, subjectively and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, subjectively and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, subjectively and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Those skilled in the art will appreciate that a user may be representative of a human user, a robotic user (e.g., computational entity), and/or substantially any combination thereof (e.g., a user may be assisted by one or more robotic agents) unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Various non-limiting embodiments are described herein as Prophetic Examples.

PROPHETIC EXAMPLES

Prophetic Example 1

An Automated Delivery System for Medical Products and Services

An automated system to provide medications, medical products and medical services is comprised of kiosks with medication dispensers, physiological sensors and a computer-based network linking the kiosks, healthcare providers, patients, and third party payers (e.g., insurance companies).

Kiosks are manufactured with a computer interface including a touchscreen monitor, a video camera, a keyboard and voice recognition capability. The kiosk also incorporates dispensers and storage for multiple medications and sensors to detect the quantity of medication delivered and to monitor the remaining inventory. Custom designed kiosks may be custom designed and adapted for example, from KIOSK Information Systems, Louisville, Colo. 80027. They may incorporate multiple component technologies including: computers, liquid crystal displays, touch screens, keyboards, card readers, biometric identity scanners, bar code scanners, printers, video cameras, and wireless transceivers (e.g., broad band, WiFi, Bluetooth and RFID).

The kiosks may contain a computer interface with a biometric identity scanner to verify the patient's identity. For example the patient interacts with a touch screen computer (e.g., iPad2 from Apple, Inc., Cupertino, Calif.) and a fingerprint sensor device (e.g., Lumidigm Venus fingerprint sensor from Lumidigm Inc., Albuquerque, N. Mex.; see Lumidigm Venus Datasheet which is incorporated herein by reference). The computer is programmed to interact verbally and by touch with the patient. The patient is prompted to touch the fingerprint sensor and the fingerprint data is compared to a database of patient medical records. Alternatively, the patient may present a credit card, insurance card or other identification to verify their identity. Payment for medication and/or services may be made at the kiosk card reader with a credit card or insurance plan debit card (e.g., Flex Plan). Payment may be included in the input received in conjunction with the subject seeking a medical product or service. The patient may also be queried verbally by the computer to verify their identity. For example, birthdate, social security number, home address, and authorization codes may be requested to gain access to the kiosk and to obtain medication or medical services. Alternatively the patient may be issued a USB flash drive by his healthcare provider which contains patient identification information and an authorization code for the kiosk as well as prescription information. Following authorization and access to the automated delivery system, the patient is photographed at the kiosk by the touch screen computer and the facial photograph is transmitted to their healthcare provider for identity verification.

A medication dispenser is integrated in the kiosk which is capable of selecting a small quantity of medication, packaging, labeling and dispensing it. For example the kiosk may dispense 30 tablets or 90 tablets of paroxetine, i.e., a 1 or 3 month's supply. Machines to dispense medications are described (see e.g., U.S. Pat. No. 8,033,424 issued to Rosenblum on Oct. 11, 2011 and U.S. Patent Application No. 2012/0303388 by Vishnubhatla et al. published on Nov. 29, 2012 which are incorporated herein by reference.) For example a pharmacy packaging machine, iPack® T60, which packages individual doses in blister packs is available from Pearson Medical Technologies, Alexandria, La. Medical products such as syringes, transdermal patches, lotions, bandages and the like may also be dispensed from the kiosk using the medication dispenser (see e.g., U.S. Pat. No. 8,033,424 Ibid.). The kiosks incorporate medication dispensers, medication storage lockers and medication inventory monitors. For example, when 30 tablets of paroxetine (30 mg tablets) are dispensed the status of paroxetine stores is updated on the kiosk computer, and if restocking is necessary an email or text message is sent alerting a pharmacy to replenish the storage locker of the specific kiosk.

The kiosks are equipped with video cameras to record dispensation of medication to a patient. Video data of the patient receiving medication is captured by the kiosk computer and transmitted to the healthcare provider (e.g., to a patient's electronic health record), to the insurer and to the patient. Moreover the video data may be accompanied by an email or text message with written details of the dispensation. For example, the email may detail: the patient's name and address, the prescription, the prescribing physician, the health insurance plan, the payment status, the cost of the medication and the date, time and kiosk location where it was dispensed. In an embodiment, the input received in conjunction with the subject seeking a medical product or service includes at least one of an authorization code, insurance code, or identification code.

The automated delivery system also provides medical services at the kiosks which include measurement, analysis and reporting of physiologic and clinical parameters to provide remote medical services and to inform prescription delivery. For example, the kiosk may contain sensors to detect key physiological parameters such as: heart rate, body temperature, respiration rate and blood oxygen level and body weight. The patient's weight may be measured by an electronic scale under the chair at the kiosk which automatically transmits the weight to a central computer containing the patient's medical record. The patient's electrocardiogram may be measured by electric potential sensors which may be placed 1 meter apart on opposite sides of the chair. Nonconductive electric potential sensors to determine a patient's electrocardiogram are described (see e.g., Harland et al., Meas. Sci. Technol. 13, 163-169, 2002 which is incorporated herein by reference). The patient's respiration rate and heart rate may be determined by a remote sensor that detects physiological activities by illuminating the patient with radio frequency (RF) electromagnetic signals and detecting the reflected electromagnetic signal waves. The sensor may be incorporated in the back of the chair. For example a remote sensor to detect respiration and heart rate is described (see e.g., U.S. Pat. No. 7,272,431 issued to McGrath on Sep. 18, 2007 which is incorporated herein by reference). The patient's body temperature is determined by thermal imaging with a radiometric camera (e.g., a 7320 ETIP camera available from Infrared Cameras, Inc., Beaumont, Tex.; see Spec. Sheet IR camera which is incorporated herein by reference). The infrared camera is installed in the kiosk and focused on the patient's forehead or eyes. Devices and methods to determine core body temperature noninvasively and remotely may be adapted from others (see e.g., U.S. Pat. No. 7,340,293 which is incorporated herein by reference).

The patient's hematocrit and blood oxygen concentration is determined by a photoplethysmograph device on the armrest of the chair. A system with a finger clip emits and detects different wavelengths of light through the tissue of the finger (see e.g., Shaltis, et al., Conf. Proc. IEEE Eng. Med. Biol. Soc. 4: 3567-3570, 2005 which is incorporated herein by reference). The extinction of selected wavelengths of light is detected and may be used to determine the hematocrit and the blood oxygen saturation value. For example, a system and method to measure hematocrit and blood oxygenation by transilluminating the patient's finger with light at wavelengths of: 660 nm, 805 nm and 1550 nm is described (see e.g., U.S. Pat. No. 5,372,136 which is incorporated herein by reference).

The biometric and physiological parameters determined remotely by the kiosk automatic data collection system are transmitted wirelessly to a central computer that communicates with health information databases (e.g., Kaiser Permanente electronic health records may be accessed using EpicCare software from Epic Systems Corp, Verona, Wis.; and Centers for Disease Control, Data and Statistics are available online at: http://www.cdc.gov/datastatistics). Wireless sensor networks for aggregating and transmitting physiological data to a central computer are described (see e.g., Gao et al., Proc. IEEE Conf. Technologies for Homeland Security, p. 187-192, 2008 which is included herein by reference).

The automated medical services include computer programs and methods to compare the patient's physiological parameters to parameters obtained from healthy individuals, to the patient's medical history and to the current prescription. The system includes a central computer with programs to correlate prescribed medications with current physiologic parameters. Computer programs to evaluate and compare physiological datasets are described (see e.g., the paper titled: OSCAR-MDA An Artificially Intelligent Advisor for Emergency Room Medicine by John L. Pollock and Devin Hosea October 1997 and available online at citeseerx.ist.psu.edu/viewdoc/download?doi=10.1.1.49.4970&rep=rep1&type=pdf. and Pollock, Cognitive Carpentry: A Blueprint for How to Build a Person, MIT Press, Cambridge, Mass., 1995 which are incorporated herein by reference).

Prophetic Example 2

Remote Delivery of Prescription Medication by an Automated Delivery System

An individual from the US is traveling in Europe for approximately 3 weeks on a business trip. After 1 week the subject loses his antidepressant medication which he requires to carry out his business and function in his daily activities. The subject's healthcare provider has established a network of kiosks in European cities which deliver medical products and services to authorized patients.

The patient obtains a supplementary amount of his antidepressant medication to last for the remaining two weeks of the trip by contacting his healthcare provider via the internet or by phone. The patient requests a supplemental prescription of antidepressant, e.g., 14 tablets of paroxetine, 30 mg each, and requests that prescription be picked up at a kiosk near his hotel in Paris. His doctor's office verifies his identity and prescription information on his medical record and authorizes dispensation of 14 tablets of paroxetine at the specified kiosk. If the patient has also lost his credit cards and other identification the doctor's office may provide him with an authorization code to allow access to the kiosk. Receipt of the medication by the patient is verified by photographs taken at the kiosk and transmitted to the healthcare provider.

Prophetic Example 3

Automated Drug Delivery System to Control Dispensation of a Controlled Substance A patient with chronic pain is prescribed, oxycodone, to control the pain and the patient receives their medication from an automated medication delivery system. Prior to prescribing oxycodone the physician may use the automated delivery system network to screen the patient. For example, the system may check the patient's name for any criminal record and it may search for any and all medical records of the patient which discuss controlled substances including prescription drugs, alcohol, or over the counter drugs. The system may also search medical records for other indicators of drug seeking behavior, i.e. frequent loss of prescriptions, frequent refill requests and seeing multiple physicians. Guidelines for prescribing opioids are available (see e.g., Substance Abuse and Mental Health Services Administration. SAMHSA Opioid Overdose Prevention Toolkit: Information for Prescribers. HHS Publication No. (SMA) 13-4742. Rockville, Md. 2013 available online at: store.samhsa.gov/shin/content//SMA13-4742/Toolkit_Prescribers.pdf which is incorporated herein by reference). Informed by the search conducted by the automated delivery system, the physician discusses an informed consent agreement with the patient. The automated delivery system can facilitate the discussion by displaying a list of topics and key information concerning oxycodone on a monitor in the doctor's office. For example, the displayed information from the informed consent agreement may include:

1) Risks and benefits of opioid therapy
2) Potential for physical dependence and cognitive impairment
3) Patient agrees to stop taking other pain medication unless recommended by physician
4) Patient agrees to obtain prescribed medication from one physician and one kiosk
5) Patient agrees to take medication according to prescribed dose and schedule
6) Patient is responsible for safeguarding supply of medication to prevent family members, friends or others from obtaining opioids Following the discussion an informed consent agreement for prescription of oxycodone (e.g., Oxycontin) may be printed from the automated medication delivery system and signed by the physician and the patient.

To help the physician execute a complete and legal prescription order according to Federal Law (see e.g., SAMHSA HHS Publication No. (SMA) 13-4742, Ibid.) the medication delivery system displays a form on the monitor requesting the required information:

Patient's name and address
Physician's name, address and DEA registration number
Electronic signature of physician
Date of issue
Name and quantity of drug prescribed
Directions for use
Refill information The completed prescription order is transmitted electronically to the pharmacy along with a designated kiosk for dispensing the medication and an authorization mode for the patient to access the medication (e.g., a fingerprint for biometric identification). For example the physician prescribes a limited amount of Oxycontin, (e.g., sufficient drug for 3-5 days) which are dispensed at a designated kiosk. To lower the risk for patient abuse of Oxycontin and/or reselling of Oxycontin the automated drug delivery system verifies the patient's identity and controls the number of refills issued to the patient according to the prescribed dose and schedule. For example the physician may prescribe: Oxycontin 10 mg every 12 hours for 3 days, i.e., 6 tablets, with a refill prescription available on day 4, day 7, and day 10 following dispensation of the first prescription. To control access to the medication delivery system and to identify the patient the kiosk may have a biometric fingerprint sensor device (e.g., Lumidigm Venus fingerprint sensor from Lumidigm Inc., Albuquerque, N. Mex.; see Lumidigm Venus Datasheet which is incorporated herein by reference).

The kiosk may have a video camera which films receipt of the Oxycontin prescription by the patient. Both events, fingerprint sensing and video recording are transmitted by the kiosk computer to the physician's office and stored in the patient's electronic medical record. Facial recognition software may be used to automatically compare the patient's photograph to the video recording obtained from the kiosk. If the facial images do not match or if the finger print identity and the facial image identity do not match an alert is sent to the physician's office and the patient's access to the kiosk is blocked until the identity discrepancies are resolved. Video data obtained by the medication delivery kiosk is transmitted to the physician's office and entered in the patient's medical record. For example, the system may ask the patient to answer questions about their chronic pain and their usage of Oxycontin prior to gaining access to a refill. Review of the video data containing the patient's responses may alert the physician to problems or to the need for additional medication. For example, the patient may require naloxone, an opioid antagonist, as a precaution for opioid overdose (see e.g., SAMHSA HHS Publication No. (SMA) 13-4742, Ibid.). The automated delivery system kiosk may request the patient via text, email or phone to make an appointment with his physician, and the system may also alert the physician to contact the patient.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
a kiosk and paired pillbox device, wherein the kiosk includes at least one sensor operably coupled to at least one computing device, wherein the at least one sensor is operable to detect one or more physiological parameters of a subject seeking a medical product or service;
the paired pillbox device being an externally coupled pillbox device including at least one compartment operably coupled to circuitry configured for sending a signal when the compartment is engaged with the at least one computing device of the kiosk;
the paired pillbox device including at least one port configured for transferring data with the at least one computing device of the kiosk,
the computing device including circuitry configured for receiving at least one input related to the subject seeking a medical product or service, the at least one input related to the subject seeking a medical product or service including the one or more physiological parameters of a subject seeking a medical product or service detected by the at least one sensor,
comparing the at least one input from the subject relating to the subject seeking a medical product or service with one or more verification datasets;
generating a verification value based on the comparison; and
dispensing the medical product or service sought directly into the paired pillbox device, upon satisfying a verification threshold; and
a subject tracking system configured to track a location of the subject relative to the paired pillbox device, wherein the computing device includes circuitry configured to provide at least one of a map or directions to a nearest kiosk that includes the medical product or service when the verification value does not satisfy the verification threshold.

2. The system of claim 1, wherein the port includes a wired connection, flash drive, microdrive, or wireless connection.

3. The system of claim 1, further including a visual, audio, or tactile indicator that the verification value has or has not satisfied the verification threshold.

4. The system of claim 1, wherein the computing device further includes circuitry for reinitiating receiving additional input related to the subject seeking a medical product or service.

5. The system of claim 4, wherein the additional input includes at least one of identification input or insurance input.

6. The system of claim 1, wherein the at least one input further includes transferring data between the pillbox device and the kiosk.

7. The system of claim 1, wherein the circuitry is configured to generate at least one of a visual cue, audio cue, or tactile cue.

8. The system of claim 1, wherein the one or more verification datasets includes one or more of an inventory dataset, an electronic medical record for the subject dataset, a verification code dataset, or a health status indicator dataset.

9. The system of claim 1, wherein the at least one input further includes at least one input from the subject in response to one or more queries.

10. The system of claim 1, wherein the one or more detected physiological parameters of the subject include at least one electrical measurement, biochemical measurement, or thermal measurement.

11. The system of claim 1, wherein the comparing at least one input includes at least one of coupling, versioning or clustering in determining the subject's verification value.

12. The system of claim 1, wherein the at least one input includes at least one input from a data storage device.

13. The system of claim 12, wherein the data storage device includes a Universal Serial Bus (USB) data storage device, CD, DVD, or other data storage device.

14. The system of claim 12, wherein the data storage device includes a mobile phone, computer tablet, computer laptop, or other computing device.

15. The system of claim 1, wherein the computing device includes circuitry configured for transmitting at least one signal to alert to a third party that a specific medical product or service has reached a pre-determined inventory level.

16. The system of claim 1, wherein the computing device includes circuitry configured for transmitting at least one signal to order inventory of one or more medical product or service that has reached a pre-determined inventory level.

17. The system of claim 1, wherein the computing device includes circuitry configured for transmitting at least one signal to order inventory of one or more medical product or service for a specific subject.

18. The system of claim 17, wherein the signal to order inventory of one or more medical product or service for a specific subject is based on a pre-determined schedule of a subject seeking the same medical product or service at one or more time points.

19. The system of claim 1, further including at least one currency exchanger.

20. The system of claim 1, further including at least one printer, scanner, or fax machine operably coupled to the computing device.

21. The system of claim 1, wherein the computing device further includes circuitry configured for transmitting a signal to send an invoice to the subject for receipt of the medical product or service.

22. The system of claim 1, further including at least one locked dispensing box containing certain pre-determined medical products or services.

23. The system of claim 22, wherein the at least one input relating to a subject's seeking a medical product or service includes a code configured to unlock the at least one locked dispensing box.

24. The system of claim 22, further including multiple locked dispensing boxes including different medical products or services accessible by the same subject.

25. The system of claim 22, wherein the at least one locked dispensing box includes circuitry configured to transmit a signal when the box is opened.

26. The system of claim 22, wherein the kiosk dispenses a key or code for the at least one locked dispensing box subsequent to satisfaction of the verification threshold.

27. The system of claim 22, wherein the code or key for the at least one locked dispensing box was previously accessible to the subject from a healthcare worker.

28. The system of claim 22, wherein the at least one locked dispensing box includes circuitry configured for transmitting a signal to order a medical product or service for re-stocking.

29. The system of claim 22, wherein the at least one locked dispensing box includes circuitry configured for transmitting a signal to alert a mobile third party to re-stock the box.

30. The system of claim 29, wherein the mobile third party includes a human or machine.

31. The system of claim 30, wherein the machine includes circuitry configured for receiving at least one signal from the locked drop box for re-stocking.

32. The system of claim 1, wherein the computing device includes circuitry configured for transmitting at least one signal to alert to a third party that a specific medical product or service has reached a pre-determined inventory level.

33. The system of claim 1, further including a locked dropbox physically coupled to the kiosk and configured to contain a medical product or service.

* * * * *